US008883989B2

(12) United States Patent
Kokkoli et al.

(10) Patent No.: US 8,883,989 B2
(45) Date of Patent: Nov. 11, 2014

(54) FRACTALKINE BINDING POLYNUCLEOTIDES AND METHODS OF USE

(71) Applicants: Efrosini Kokkoli, Edina, MN (US); Brett M. Waybrant, Minneapolis, MN (US); Srinand Sreevatsan, Roseville, MN (US); Ping Wang, Shoreview, MN (US)

(72) Inventors: Efrosini Kokkoli, Edina, MN (US); Brett M. Waybrant, Minneapolis, MN (US); Srinand Sreevatsan, Roseville, MN (US); Ping Wang, Shoreview, MN (US)

(73) Assignee: Regents of The University of Minnesota, St. Paul, MN (US)

( * ) Notice: Subject to any disclaimer, the term of this patent is extended or adjusted under 35 U.S.C. 154(b) by 0 days.

(21) Appl. No.: 13/655,155

(22) Filed: Oct. 18, 2012

(65) Prior Publication Data
US 2013/0123347 A1 May 16, 2013

Related U.S. Application Data

(60) Provisional application No. 61/548,557, filed on Oct. 18, 2011.

(51) Int. Cl.
*C12N 15/11* (2006.01)
*C12N 15/115* (2010.01)

(52) U.S. Cl.
CPC ........ *C12N 15/115* (2013.01); *C12N 2310/351* (2013.01); *C12N 2310/16* (2013.01)
USPC .............................. 536/23.1; 424/450; 514/44

(58) Field of Classification Search
USPC .............................. 536/23.1; 514/44; 424/450
See application file for complete search history.

(56) References Cited

U.S. PATENT DOCUMENTS

| | | | |
|---|---|---|---|
| 5,013,556 A | 5/1991 | Woodle et al. | |
| 5,891,468 A | 4/1999 | Martin et al. | |
| 5,932,539 A | 8/1999 | Stupp et al. | |
| 8,435,993 B2 * | 5/2013 | Fatatis et al. | 514/250 |
| 2002/0054875 A1 | 5/2002 | Koch et al. | |
| 2002/0055456 A1 | 5/2002 | Koch | |
| 2002/0192212 A1 | 12/2002 | Imai et al. | |
| 2003/0118595 A1 * | 6/2003 | Niemeyer et al. | 424/184.1 |
| 2005/0048110 A1 | 3/2005 | Discher et al. | |
| 2006/0240009 A1 | 10/2006 | Zalipsky et al. | |
| 2007/0277269 A1 * | 11/2007 | Alexandrov et al. | 800/290 |

FOREIGN PATENT DOCUMENTS

| | | | | |
|---|---|---|---|---|
| EP | 1 520 586 A1 | 4/2005 | | |
| EP | 1852508 | * 7/2007 | ............. | C12N 15/31 |
| EP | 1 875 923 A2 | 1/2008 | | |
| WO | WO 2005/030245 | * 4/2005 | ............. | A61K 38/17 |

OTHER PUBLICATIONS

Kokkoli et al, Biomacromol. 6:1272-1279, 2005.*
Joshi et al, Mol. & Cell. Probes 23: 20-28, 2009.*
Deshpande et al, AC152066; 2009.*
Farokhzad et al, Cancer Res. 64:7668-7672, 2004.*
Ewing et al, GenBank FR830963.1; Mar. 10, 2011.*
Ahn et al., "Tumor necrosis factor-alpha induces fractalkine expression preferentially in arterial endothelial cells and mithramycin A suppresses TNF-alpha-induced fractalkine expression," *American Journal of Pathology*, May 2004; 164(5):1663-1672.
Ancuta et al., "CD16(+) monocytes produce IL-6, CCL2, and matrix metalloproteinase-9 upon interaction with CX3CL1-expressing endothelial cells," *Journal of Leukocyte Biology*, 2006; 80:1156-1164.
Baldrich et al., "Aptasensor development: Elucidation of critical parameters for optimal aptamer performance," *Anal. Chem.*, Dec. 2004; 76:7053-7063.
Bazan et al., "A new class of membrane-bound chemokine with a $CX_3C$ motif," *Nature*, 1997; 385:640-644.
Brody et al., "The use of aptamers in large arrays for molecular diagnostics," *Mol. Diagn.*, 1999; 4:381-388.
Brueckmann et al., "Therapeutic potential of fractalkine: a novel approach to metastatic colon cancer," *Gut*, 2007; 56:314-316.
Bunka et al., "Aptamers come of age—at last," *Nature Rev. Microbiol.*, 2006; 4:588-596.
Cao et al., "Reversible Cell-Specific Drug Delivery with Aptamer-Functionalized Liposomes," *Angew. Chem. Int. Ed.*, 2009; 48:6494-6498.
Cerchia et al., "Targeting cancer cells with nucleic acid aptamers," *Trends in Biotechnol.*, 2010; 28:517-525.
Chen et al., "In vivo inhibition of CC and CX3C chemokine-induced leukocyte infiltration and attenuation of glomerulonephritis in Wistar-Kyoto (WKY) rats by vMIP-II," *Journal of Experimental Medicine*, 1998; 188:193-198.
Ciesiolka et al., "Affinity selection-amplification from randomized ribooligonucleotide pools," *Method Enzymol.*, 1996; 267:315-335.
Combadiere et al., "Identification of CX3CR1—achemotactic receptor for the human CX3C chemokine fractalkine and a fusion coreceptor for HIV-1," *J. Biol. Chem.*, 1998; 273:23799-23804.
Conrad et al., "In vitro selection of nucleic acid aptamers that bind proteins," *Method Enzymol.*, 1996:336-367.
Damas et al., "Expression of fractalkine (CX3CL1) and its receptor, CX3CR1, is elevated in coronary artery disease and is reduced during statin therapy," *Arteriosclerosis Thrombosis and Vascular Biology*, 2005; 25:2567-2572.
Deisingh et al., "Biosensors for the detection of bacteria," *Can. J. Microbiol.*, 2004; 50:69-77.
D'Hause et al., "Fractalkine/CX3CR1: why a single chemokine-receptor duo bears a major and unique therapeutic potential," *Expert Opin. Ther. Targets*, 2010; 14:207-219.

(Continued)

*Primary Examiner* — Kevin Hill
(74) *Attorney, Agent, or Firm* — Mueting, Raasch & Gebhardt, P.A.

(57) ABSTRACT

Provided herein are polynucleotides that bind to fractalkine. In one embodiment, a polynucleotide includes the polynucleotide sequence SEQ ID NO:1 or a sequence having at least 80% identity to SEQ ID NO:1. Also provided herein are structures that include such a polynucleotide present on its surface, including 2-dimentional and 3-dimentional structures. Also provided are compositions that include such a polynucleotide, and methods for using the polynucleotides.

23 Claims, 17 Drawing Sheets

(56) References Cited

OTHER PUBLICATIONS

Dieleman et al., "Dextran sulfate sodium-induced colitis occurs in severe combined immunodeficient mice,"*Gastroenterol.*, 1994; 107(6):1643-1652.

Dimberg et al., "Polymorphisms of Fractalkine receptor CX3CR1 and plasma levels of its ligand CX3CL1 in colorectal cancer patients," *Int. J. Colorectal Dis.*, 2007; 22:1195-1200.

Drolet et al., "A high throughput platform for systematic evolution of ligands by exponential enrichment (SELEX).," *Comb Chem High Throughput Screen*, 1999; 2(5):271-278.

Ellington et al., "In vitro selection of RNA molecules that bind specific ligands," *Nature*, Aug. 1990; 346:818-822.

Erreni et al., "Human glioblastoma tumours and neural cancer stem cells express the chemokine CX3CL1 and its receptor CX3CR1," *Eur. J. Cancer*, 2010; 46:3383-3392.

Farokhzad et al., "Targeted nanoparticle-aptamer bioconjugates for cancer chemotherapy in vivo," *Proc. Natl. Acad. Sci. USA*, 2006; 103:6315-6320.

Fong et al., "Fractalkine and CX3CR1 mediate a novel mechanism of leukocyte capture, firm adhesion, and activation under physiologic flow," *J. Exp. Med.*, 1998; 188:1413-1419.

Fong et al., "Ultrastructure and Function of the Fractalkine Mucin Domain in CX3C Chemokine Domain Presentation," *J. Biol Chem.*, 2000; 275 :3781-3786.

Fujimoto et al., "Interferon-gamma stimulates fractalkine expression in human bronchial epithelial cells and regulates mononuclear cell adherence," *Cell Mol. Biol.*, 2001; 25:233-238.

Garg et al., "Targeting colon cancer cells using PEGylated liposomes modified with a fibronectin-mimetic peptide," *Int. J. Pharm.*, 2009; 366:201-210.

Garton et al., "Tumor Necrosis Factor-α-converting Enzyme (ADAM17) Mediates the Cleavage and Shedding of Fractalkine (CX3CL1)," *J. Biol Chem.*, 2001; 276:37993-38001.

Gaudin et al., "Identification of the Chemokine CX3CL1 as a New Regulator of Malignant Cell Proliferation in Epithelial Ovarian Cancer," *PLoS One*, Jul. 2011; 6(7):e21546.

Gu et al., "Targeted nanoparticles for cancer therapy," *Nano Today*, 2007; 2:14-21.

Guo et al., "Chemoattraction, adhesion and activation of natural killer cells are involved in the antitumor immune response induced by fractalkine/CX3CL1," *Immunology Letters*, 2003; 89:107.

Guo et al., "Fractalkine transgene induces T-cell-dependent antitumor immunity through chemoattraction and activation of dendritic cells," *International Journal of Cancer*, 2003; 103:212-220.

Harrison et al., "Role for neuronally derived fractalkine in mediating interactions between neurons and CX3CR1expressing microglia," *Proc. Natl. Acad. Sci. USA*, 1998; 95:10896-10901.

Harrison et al., "Inflammatory agents regulate in vivo expression of fractalkine in endothelial cells of the rat heart," *J. Leukoc. Biol.*, 1999; 66:937-944.

Hartgerink et al., "Peptide-amphiphile nanofibers: A versatile scaffold for the preparation of self-assembling materials," *PNAS USA*, 2002; 99:5133-5138.

Haskell et al., "Molecular uncoupling of fractalkine-mediated cell adhesion and signal transduction: rapid flow arrest of CX3CR1-expressing cells is independent of G-protein activation," *J. Biol. Chem.*, 1999; 274:10053-10058.

Haskell et al., "Targeted deletion of $CX_3CR1$ reveals a role for fractalkine in cardiac allograft rejection," *J. Clin. Invest.*, 2001; 108:679-688.

Hermann et al., "Adaptive recognition by nucleic acid aptamers," *Science*, 2000; 287:820-825.

Hesselberth et al., "In vitro selection of nucleic acids for diagnostic applications," *J. Biotechnol.*, 2000; 74:15-25.

Holmes et al., "Intra-neural administration of fractalkine attenuates neuropathic pain-related behaviour," *J. Neurochem.*, 2008; 106:640-649.

Hundhausen et al., "The disintegrin-like metalloproteinase ADAM10 is involved in constitutive cleavage of CX3CL1 (fractalkine) and regulates CX3L1-mediated cell-cell adhesion," *Blood*, 2003; 102:1186-1195.

Hyakudomi et al., "Increased expression of fractalkine is correlated with a better prognosis and an increased number of both CD8+ T cells and natural killer cells in gastric adenocarcinoma.," *Ann Surg Oncol.*, 2008; 15:1775-1782.

Imai et al., "Identification and molecular characterization of fractalkine receptor CX3CR1, which mediates both leukocyte migration and adhesion," *Cell*, 1997; 91:521-530.

Irvine et al., "Selexion—systematic evolution of ligands by exponential enrichment with integrated optimization by nonlinear-analysis," *J. Mol. Biol.*, 1991; 222:739-761.

Ishida et al., "Liposome Clearance," *Bioscience Reports*, 2002; 22(2):197-224.

Jamieson et al., "CX3CR1 is expressed by prostate epithelial cells and androgens regulate the levels of CX3CL1/fractalkine in the bone marrow: Potential role in prostate cancer bone tropism," *Cancer Research*, 2008; 68:1715-1722.

Jayasena, "Aptamers: An emerging class of molecules that rival antibodies in diagnostics," *Clin. Chem.*, 1999; 45:1628-1650.

Jenison et al., "High-resolution molecular discrimination by RNA," *Science*, 1994; 23:1425-1429.

Johnston et al., "A Role for Proinflammatory Cytokines and Fractalkine in Analgesia, Tolerance, and Subsequent Pain Facilitation Induced by Chronic Intrathecal Morphine," *J. Neurosci.*, 2004; 24(33):7353-7365.

Julia, "CX3CL1 in allergic diseases: not just a chemotactic molecule," *Allergy*, Sep. 2012; 67:1106-1110.

Kang et al., "A liposome-based nanostructure for aptamer directed delivery," *Chem. Commun.*, 2010; 46:249-251.

Lavergne et al., "Fractalkine mediates natural killer-dependent antitumor responses in vivo," *Cancer Research*, 2003; 63:7468-7474.

Lee et al., "A therapeutic aptamer inhibits angiogenesis by specifically targeting the heparin binding domain of VEGF(165)," *Proc. Natl Acad. Sci. USA*, 2005; 102:18902-18907.

Lee et al., "Aptamer therapeutics advance," *Curr. Opin. Chem. Biol.*, 2006; 10:282-289.

Liu et al., "Recycling of the membrane-anchored chemokine, $CX_3CL1$," *Journal of Biological Chemistry*, 2005; 280:19859-19866.

Lucas et al., "The transmembrane form of the CX3CL1 chemokine fractalkine is expressed predominantly by epithelial cells in vivo," *American Journal of Pathology*, 2001; 158:855-866.

Lupold et al., "Identification and characterization of nuclease-stabilized RNA molecules that bind human prostate cancer cells via the prostate-specific membrane antigen," *Cancer Res.*, 2002; 62:4029-4033.

"Macugen," http://www.macugen.com/, Retrieved from the Internet Nov. 19, 2013; Copyright 2013, Valeant Pharmaceuticals North America LLC, Bridgewater, NJ.

Matloubian et al., "A transmembrane CXC chemokine is a ligand for HIV-coreceptor Bonzo," *Nat. Immunol.*, 2000; 1:298-304.

Matsubara et al., "Fractalkine-CX3CR1 axis regulates tumor cell cycle and deteriorates prognosis after radical resection for hepatocellular carcinoma," *J. Surg. Oncol.*, 2007; 95:241-249.

Michaud et al., "A DNA aptamer as a new target-specific chiral selector for HPLC," *J. Am. Chem. Soc.*, 2003; 125:8672-8679.

Milligan et al., "Evidence that exogenous and endogenous fractalkine can induce spinal nociceptive facilitation in rats," *Eur. J. Neurosci.*, 2004; 20:2294-2302.

Missailidis et al., "Selection of aptamers with high affinity and high specificity against C595, an anti-MUC1 IgG3 monoclonal antibody, for antibody targeting," *J. Immunol. Meth.*, 2005; 296:45-62.

Murphy et al., "An improved method for the in vitro evolution of aptamers and applications in protein detection and purification," *Nucl. Acids Res.*, 2003; 31(18):e110.

Murphy et al., "Fractalkine in rheumatoid arthritis: a review to date," *Rheumatology*, 2008; 47:1446-1451.

National Center for Biotechnology Information, National Library of Medicine, National Institutes of Health, GenBank Locus X3CL1_Human, Accession No. P78423, "RecName: Full=Fractalkine; AltName: Full=C-X3-C motif chemokine 1; AltName: Full=CX3C membrane-anchored chemokine; AltName: Full=Neurotactin; AltName: Full=Small-inducible cytokine D1; Contains: RecName: Full=Processed fractalkine; Flags: Precursor," [online]. Bethesda,

(56) References Cited

OTHER PUBLICATIONS

MD [retrieved on Oct. 21, 2013]. Retrieved from the Internet:<http://www.ncbi.nlm.nih.gov/protein/P78423>; 7 pgs.
Ng et al., "Pegaptanib, a targeted anti-VEGF aptamer for ocular vascular disease," *Nature Rev. Drug Discov.*, 2006; 5:123-132.
Nukiwa et al., "Dendritic cells modified to express fractalkine/CX3CL1 in the treatment of pre-existing tumors," *European Journal of Immunology*, 2006; 36:1019-1027.
Ohta et al., "The high expression of fractalkine results in a better prognosis for colorectal cancer patients," *Inter. J. Oncology*, 2005; 26:41-47.
Papahadjopoulos et al., "Liposomes by Design," Janoff, (Ed.), Marcel Dekker, New York, 1999:1-12.
Pestourie et al., "Aptamers against extracellular targets for in vivo applications," *Biochimie*, 2005; 87:921-930.
Robinson et al., "A role for fractalkine and its receptor ($CX_3CR1$) in cardiac allograft rejection," *J. Immunol.*, 2000; 165:6067-6072.
Ruckman et al., "2'-fluoropyrimidine RNA-based aptamers to the 165-amino acid form of vascular endothelial growth factor (VEGF(165))—Inhibition of receptor binding and VEGF-induced vascular permeability through interactions requiring the exon 7-encoded domain," *J. Biol. Chem.*, 1998; 273-20556-20567.
Ruth et al., "Fractalkine, a novel chemokine in rheumatoid arthritis and in rat adjuvant-induced arthritis," *Arthritis Rheum.*, 2001; 44:1568-1581.
Savran et al., "Micromechanical detection of proteins using aptamer-based receptor molecules," *Anal. Chem.* 2004; 76:3194-3198.
Schneider et al., "Selection of high-affinity RNA ligands to the bacteriophage-R17 coat protein," *J. Mol. Biol.*, 1992; 228:862-869.
Shulby et al., "$CX_3CR1$-fractalkine expression regulates cellular mechanisms involved in adhesion, migration, and survival of human prostate cancer cells," *Cancer Research*, 2004; 64:4693-4698.
Simoes et al., "On the formulation of pH-sensitive liposomes with long circulation times," *Adv. Drug Deliv. Rev.*, 2004; 56(7):947-965.
Stoltenburg et al., "SELEX—A (r)evolutionary method to generate high-affinity nucleic acid ligands," *Biomolecular Engineering*, 2007; 24:381-403.
Sun et al., "New evidence for the involvement of spinal fractalkine receptor in pain facilitation and spinal glial activation in rat model of monoarthritis," *Pain*, 2007; 129:64-75.
Takemura et al., "DNA aptamers that bind to PrPC and not PrPSc show sequence and structure specificity," *Exp. Biol. Med.*, 2006; 231:204-214.
Tamura et al., "MEGA5: Molecular Evolutionary Genetics Analysis using Maximum Likelihood, Evolutionary Distance, and Maximum Parsimony Methods," *Mol. Biol. Evolution*, May 4, 2011; 28:2731-2739.
Torchilin, "Drug Targeting," *Eur. J. Pharm. Sci.*, 2000; 11:S81-S91.
Tuerk et al., "Systematic Evolution of Ligands by Exponential Enrichment—RNA Ligands to Bacteriophage-T4 DNA-Polymerase," *Science*; 1990; 249:505-510.
Ulrich et al., "DNA and RNA aptamers: From tools for basic research towards therapeutic applications," *Comb. Chem. High Throughput Screen*, 2006; 9:619-632.
Umehara et al., "Fractalkine in vascular biology—From basic research to clinical disease," *Arteriosclerosis Thrombosis and Vascular Biology*, 2004; 24:34-40.
Vinores, "Technology evaluation: Pegaptanib, Eyetech/Pfizer," *Curr. Opin. Mol. Ther.* 2003; 5:673-679.
Vinores, "Pegaptanib in the treatment of wet, age-related macular degeneration," *Int. J. Nanomed.*, 2006; 1:263-268.
Vitale et al., "Tissue-specific differential antitumor effect of molecular forms of fractalkine in a mouse model of metastatic colon cancer," *Gut*, 2007; 56:365-372.
Waybrant et al., "Development of Aptamer-Amphiphiles for Targeted Delivery to Colon Cancer Cells Expressing Fractalkine," Presentation Abstract, *Proceedings of the 2011 AIChE Annual Meeting*, Minneapolis, MN; Oct. 19, 2011.
Willis et al., "Liposome anchored vascular endothelial growth factor aptamers," *Bioconjugate Chem.*, 1998; 9:573-582.
Zeng et al., "Fractalkine (CX3CL1)- and Interleukin-2-Enriched Neuroblastoma Microenvironment Induces Eradication of Metastases Mediated by T Cells and Natural Killer Cells," *Cancer Res.*, 2007; 67:2331-2338.

\* cited by examiner

SEQUENCE LISTING

<160> NUMBER OF SEQ ID NOS: 9

<210> SEQ ID NO 1
<211> LENGTH: 40
<212> TYPE: DNA
<213> ORGANISM: artificial
<220> FEATURE:
<223> OTHER INFORMATION: FKN-S2 polynucleotide having fractalkine
      binding activity

<400> SEQUENCE: 1
ggggtgggtg gggggcacgt gtgggggcgg ccagggtgct 40

<210> SEQ ID NO 2
<211> LENGTH: 40
<212> TYPE: DNA
<213> ORGANISM: artificial
<220> FEATURE:
<223> OTHER INFORMATION: polynucleotide having fractalkine binding activity

<400> SEQUENCE: 2
ggggtrrryr rrrrryryry ryrrrrryrr yyrrrgtgct 40

<210> SEQ ID NO 3
<211> LENGTH: 40
<212> TYPE: DNA
<213> ORGANISM: artificial
<220> FEATURE:
<223> OTHER INFORMATION: polynucleotide having fractalkine binding activity
<220> FEATURE:
<221> NAME/KEY: misc_feature
<223> OTHER INFORMATION: n is any nucleotide
<220> FEATURE:
<221> NAME/KEY: misc_feature
<222> LOCATION: (6)..(35)
<223> OTHER INFORMATION: n is a, c, g, or t

<400> SEQUENCE: 3
ggggtnnnnn nnnnnnnnnn nnnnnnnnnn nnnnngtgct 40

<210> SEQ ID NO 4
<211> LENGTH: 40
<212> TYPE: DNA
<213> ORGANISM: artificial
<220> FEATURE:
<223> OTHER INFORMATION: random 40-mer control polynucleotide

<400> SEQUENCE: 4
ctatcggcga catgaacttt ggcaagggca tctggtccat 40

<210> SEQ ID NO 5
<211> LENGTH: 78
<212> TYPE: DNA
<213> ORGANISM: artificial
<220> FEATURE:
<223> OTHER INFORMATION: aptamer library sequence
<220> FEATURE:
<221> NAME/KEY: misc_feature
<222> LOCATION: (19)..(58)
<223> OTHER INFORMATION: n is any nucleotide

<400> SEQUENCE: 5
gtgcagtcaa agacgtccnn nnnnnnnnnn nnnnnnnnnn nnnnnnnnnn nnnnnnnnga 60
ccatgaagtg cgattgcc 78

-continued

```
<210> SEQ ID NO 6
<211> LENGTH: 18
<212> TYPE: DNA
<213> ORGANISM: artificial
<220> FEATURE:
<223> OTHER INFORMATION: synthetic oligonucleotide primer

<400> SEQUENCE: 6
gtgcagtcaa agacgtcc                                                   18

<210> SEQ ID NO 7
<211> LENGTH: 40
<212> TYPE: DNA
<213> ORGANISM: artificial
<220> FEATURE:
<223> OTHER INFORMATION: scrambled FKN-S2 aptamer

<400> SEQUENCE: 7
gttgggatga gggtgggcgg gcgcggcggc tgggggtcgg                           40

<210> SEQ ID NO 8
<211> LENGTH: 20
<212> TYPE: DNA
<213> ORGANISM: artificial
<220> FEATURE:
<223> OTHER INFORMATION: synthetic oligonucleotide primer

<400> SEQUENCE: 8
ggcaatcgca cttcatggtc                                                 20

<210> SEQ ID NO 9
<211> LENGTH: 50
<212> TYPE: DNA
<213> ORGANISM: artificial
<220> FEATURE:
<223> OTHER INFORMATION: 10T FKN-S2 aptamer-amphiphile

<400> SEQUENCE: 9
ggggtgggtg gggggcacgt gtggggcgg ccagggtgct tttttttttt                 50
```

FRACTALKINE BINDING POLYNUCLEOTIDES AND METHODS OF USE

CROSS-REFERENCE TO RELATED APPLICATIONS

This application claims the benefit of U.S. Provisional Application Ser. No. 61/548,557, filed Oct. 18, 2011, which is incorporated by reference herein.

GOVERNMENT FUNDING

This invention was made with government support under CBET-0846274 awarded by the National Science Foundation. The government has certain rights in the invention.

SEQUENCE LISTING

This application contains a Sequence Listing electronically submitted via EFS-Web to the United States Patent and Trademark Office as an ASCII text filed entitled "110-03570101_SubstituteSequenceListing_ST25.txt" having a size of 3 kilobytes and created on Jan. 21, 2014. The information contained in the Sequence Listing is incorporated by reference herein.

BACKGROUND

Fractalkine, or $CX_3CL1$, is a member of the chemokine family having a unique structure and a central role in human inflammatory diseases and cancer (D'Haese et al., 2010, *Expert Opin Ther Targets*, 14:207-219). Currently no therapeutics targeting fractalkine exist. Fractalkine is one of two chemokines, along with CXCL16, that exist in two active forms, membrane bound and soluble (Matloubian et al., 2000, *Nat. Immunol.*, 1:298-304). Membrane bound fractalkine captures circulating leukocytes through integrin independent binding with its highly specific receptor $CX_3CR1$ expressed on leukocytes (Imai et al., 1997, *Cell*, 91:521-530, Haskell et al., 1999, *J Biol Chem*, 274:10053-10058). Fractalkine's structure facilitates leukocyte adhesion. Binding occurs exclusively through the chemokine domain of fractalkine that sits atop a heavily glycosylated mucin-like stalk that extends the chemokine domain approximately 29 nm away from the cell membrane to increase accessibility (Fong et al., 2000, *J Biol Chem*, 275:3781-3786). The soluble form is produced by cleavage of membrane bound fractalkine near the cell membrane by the metalloproteinases ADAM10 and ADAM17 and is a potent chemoattractant for natural killer cells, monocytes and subsets of T-cells (Bazan et al., 1997, *Nature*, 385:640-644, Garton et al., 2001, *J Biol Chem*, 276:37993-38001, Hundhausen et al., 2003, *Blood*, 102:1186-1195).

Fractalkine is expressed by many cancer tissues including human gioblastoma (Erreni et al., 2010, *Eur J Cancer*, 46:3383-3392), hepatocellular carcinoma (Matsubara et al., 2007, *J Surg Oncol*, 95:241-249), neuroblastoma (Zeng et al., 2007, *Cancer Res*, 67:2331-2338), epithelial ovarian cancer (Gaudin et al., 2011, *PLoS ONE*, 6:e21546), colorectal cancer (Ohta et al., 2005, *Int J Oncol*, 26:41-47), and gastric adenocarcinoma (Hyakudomi et al., 2008, *Ann Surg Oncol*, 15:1775-1782) causing an increased leukocyte presence resulting in an antitumor effect. Furthermore, fractalkine has been implicated in many inflammatory diseases primarily through the recruitment and adhesion of leukocytes mediating the body inflammatory response (D'Haese et al., 2010, *Expert Opin Ther Targets*, 14:207-219). Anti-fractalkine antibodies reduce arthritic symptoms in mouse models and elimination of fractalkine from synovial fluid reduces angiogenesis suggesting inhibition of fractalkine may be a treatment for rheumatoid arthritis (Murphy et al., 2008, *Rheumatology*, 47:1446-1451). Fractalkine also appears to play a role in allergic diseases, such as asthma, and local administration of fractalkine antagonist to antigen-sensitized mice resulted in reduced airway hyper-responsiveness and airway inflammation (Julia, 2012, *Allergy*, 67:1106-1110).

Other attempts to develop a fractalkine binding molecule include a peptide ligand that bound fractalkine but lacked sufficient affinity for cellular applications (Kokkoli et al., 2005, *Biomacromolecules*, 6:1272-1279).

SUMMARY OF THE INVENTION

The present invention provides polynucleotides that bind to fractalkine. In one embodiment, a polynucleotide includes the polynucleotide sequence SEQ ID NO:1 or a sequence having at least 80% identity to SEQ IN NO: 1. In one embodiment, a polynucleotide may bind to human fractalkine with a $K_D$ of less than 40 nM, and in one embodiment, with a $K_D$ of less than 1 nM. The polynucleotide may be a single stranded deoxyribonucleic acid. The polynucleotide may include at least one modification, such as a modification of a nucleic acid sugar, base, backbone, or combination thereof. The polynucleotide may include a covalently attached tail, and it may be at the 5' end, the 3' end, and/or it may be covalently attached to one or more internal nucleotides. In one embodiment, the tail may include an affinity label, such as biotin or avidin. In one embodiment, the tail may include a hydrophilic group, such as PEG, including two or more PEG molecules. In one embodiment, the tail may include a hydrophobic group. In one embodiment, the tail may include an amphiphile. In one embodiment, the tail may include a drug or an imaging agent.

Also provided herein is a surface that includes a polynucleotide that binds to fractalkine. In one embodiment, the surface is 2-dimensional, and in one embodiment, the surface is 3-dimensional. In one embodiment, the surface is part of a vesicle or a scaffold, such as a gel.

Also provided herein is a composition that includes a polynucleotide that binds to fractalkine and a pharmaceutically acceptable carrier. Also provided herein is a method that includes administering the composition to a subject, such as a human.

Also provided herein is a 3-dimensional structure that includes one or more surfaces, wherein at least one of the surfaces includes an attached polynucleotide that binds fractalkine. In one embodiment, the surface is a layer, and may include a lipid, or a polymer, such as a hydrophilic polymer. In one embodiment, the attachment between the polynucleotide and the surface is covalent.

Also provided herein is a method for identifying a polynucleotide that binds to fractalkine. The method may include contacting a mixture of polynucleotides with fractalkine, wherein polynucleotides having increased affinity to the fractalkine faun polynucleotide-fractalkine complexes, and partitioning the increased affinity polynucleotide from the remainder of the mixture, to result in two differentiable polynucleotide pools, wherein the polynucleotides in each pool have different relative affinities to the fractalkine. The increased affinity polynucleotides are amplified to yield a ligand-enriched mixture of polynucleotides, whereby polynucleotide ligands of the fractalkine may be identified.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
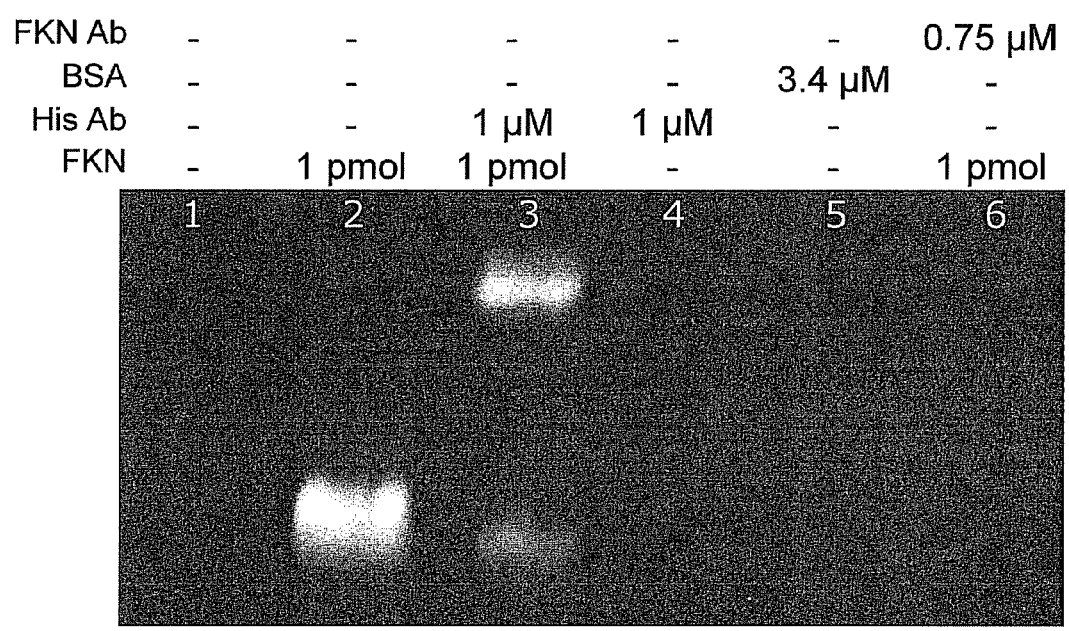
FIG. 1. EMSA analysis of the 12$^{th}$ SELEX round. Lane 1: Aptamer with no FKN. Unbound aptamer band removed for brevity. See full figure at FIG. 6. Lane 2: Aptamer with FKN. Lane 3: Addition of the His Ab causes a supershift. Lane 4: The aptamer does not bind the His Ab. Lane 5: The aptamer does not bind bovine serum albumin (BSA). Lane 6: An anti-chemokine domain antibody blocks aptamer binding. All lanes have 5 nM aptamer concentration.

Provided herein are polynucleotides that will specifically bind fractalkine, a polypeptide that is present on the surface of inflamed endothelial cells or certain cancer cells. A polynucleotide that specifically binds fractalkine has fractalkine binding activity. Fractalkine binding activity, also referred to herein as biological activity, is described in greater detail here. As used herein, the term "polynucleotide" refers to a polymeric form of nucleotides of any length, either ribonucleotides or deoxynucleotides, and includes both double- and single-stranded DNA and RNA. A polynucleotide of the present invention may also be referred to herein as an aptamer. A polynucleotide can be prepared with the aid of recombinant, enzymatic, or chemical techniques. A polynucleotide can be linear or circular in topology. A polynucleotide can be, for example, a portion of a vector, such as an expression or cloning vector, or a fragment. Polynucleotides that are artificially produced, e.g., through chemical or recombinant means, are considered to be isolated.

An example of a polynucleotide having fractalkine binding activity includes the 40 nucleotide sequence GGGGTGGGTGGGGGGCACGT-GTGGGGGCGGCCAGGGTGCT (SEQ ID NO:1). A polynucleotide having fractalkine binding activity is a single-stranded molecule with secondary structures facilitating binding to fractalkine. A polynucleotide may be single stranded DNA, single stranded RNA, or a combination thereof. The skilled person understands that an RNA molecule will include uracil nucleotides in place of thymine. Examples of other polynucleotides include those having sequence similarity with the nucleotide sequence of SEQ ID NO:1. Sequence similarity of two polynucleotides can be determined by aligning the residues of the two polynucleotides (for example, a candidate polynucleotide and SEQ ID NO:1) to optimize the number of identical nucleotides along the lengths of their sequences; gaps in either or both sequences are permitted in making the alignment in order to optimize the number of identical nucleotides, although the nucleotides in each sequence must nonetheless remain in their proper order. A candidate polynucleotide is the polynucleotide being compared to SEQ ID NO:1, the reference polynucleotide. A candidate polynucleotide may be produced using recombinant techniques, or chemically or enzymatically synthesized.

Unless modified as otherwise described herein, a pair-wise comparison analysis of nucleotide sequences can be carried out using the Blastn program of the BLAST search algorithm, available through the World Wide Web, for instance at the internet site maintained by the National Center for Biotechnology Information, National Institutes of Health. Preferably, the default values for all Blastn search parameters are used. Alternatively, sequence similarity may be determined, for example, using sequence techniques such as GCG FastA (Genetics Computer Group, Madison, Wis.), MacVector 4.5 (Kodak/IBI software package) or other suitable sequencing programs or methods known in the art.

Thus, as used herein, a polynucleotide disclosed herein having fractalkine binding activity includes those with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleotide sequence identity to SEQ ID NO:1.

In one embodiment a polynucleotide disclosed herein having fractalkine binding activity includes the nucleotide sequence GGGGTRRRYRRRRRRYRYRYRYR-RRRRYRRYYRRRGTGCT (SEQ ID NO:2), where R is a purine and Y is a pyrimidine. In one embodiment a polynucleotide disclosed herein having fractalkine binding activity includes the nucleotide sequence GGGGT$N_{30}$GTGCT (SEQ ID NO:3), where N is any nucleotide.

In one embodiment a polynucleotide having fractalkine binding activity includes less than 40 nucleotides, e.g., less than the 40 nucleotides of SEQ ID NO:1 or less than 40 nucleotides of a polynucleotide having sequence identity to SEQ ID NO:1. In one embodiment, such a polynucleotide may have a deletion of nucleotides from the 5' end. In one embodiment, such a polynucleotide may have a deletion of nucleotides from the 3' end. In one embodiment, such a polynucleotide may have a deletion of internal nucleotides. In one embodiment, the number of nucleotides missing from either the 5' end, the 3' end, internally, or a combination thereof, may be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, and so on, up to 30. In one embodiment, the number of nucleotides missing from either the 5' end, the 3' end, or internally may be 1, 2, 3, 4, 5, 6, 7, 8, 9, 10, 11, 12, 13, 14, 15, 16, 17, 18, 19, 20, and so on, up to 30.

In one embodiment a polynucleotide having fractalkine binding activity includes greater than 40 nucleotides, e.g., additional nucleotides are present at the 5' end, the 3' end, or both the 5' and 3' end. In one embodiment a polynucleotide having fractalkine activity includes additional nucleotides internally, e.g., additional nucleotides are present between the first and the 40th nucleotide.

The fractalkine binding activity of a polynucleotide disclosed herein, including a compound that includes such a polynucleotide, refers to the ability to specifically bind the chemokine domain of fractalkine. As used herein, a polynucleotide that can "specifically bind" a fractalkine is a polynucleotide that will, under the appropriate conditions, interact with fractalkine, such as the chemokine domain of fractalkine, even in the presence of a diversity of potential binding targets. Methods for determining whether a polynucleotide specifically binds to the chemokine domain of fractalkine are routine and known in the art, and one example is described in Example 1. An example of a suitable fractalkine that can be used to measure fractalkine binding activity is a human fractalkine available from R&D Systems (Catalog Number 365-FR-025, Minneapolis, Minn.). Another example of a suitable fractalkine that can be used to measure fractalkine binding activity is disclosed at amino acids 25-339 of Genbank accession number P78423. The specificity of a polynucleotide for fractalkine may be determined by use of an anti-chemokine domain antibody to block binding. Such an assay is described in Example 1. Anti-chemokine domain antibody that can be used for such a test is commercially available from, for instance, R&D Systems (Catalog Number AF365). In one embodiment, a polynucleotide has a half maximal inhibitory concentration ($IC_{50}$) for the chemokine domain of fractalkine of less than 150 nM, less than 100 nM, less than 80 nM, less than 60 nM, less than 40 nM, less than 10 nM, less than 1 nM, less than 0.1 nM, or less than 0.01 nM. In one embodiment, a polynucleotide has a dissociation constant ($K_D$) for the chemokine domain of fractalkine of less than 150 nM, less than 100 nM, less than 80 nM, less than 60 nM, less than 40 nM, less than 10 nM, less than 1 nM, less than 0.1 nM, or less than 0.01 nM. In one embodiment, the dissociation constant is 30 nM.

Polynucleotides of the present invention may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A polynucleotide of the present invention can include modifications at one or more of the nucleic acids present in the polynucleotide.

Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-dimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. Polynucleotides can be obtained commercially synthesized to include such modifications (for instance, Dharmacon Inc., Lafayette, Colo.).

Polynucleotides of the present invention can be produced in vitro or in vivo. For instance, methods for in vitro synthesis include, but are not limited to, chemical synthesis with a conventional DNA/RNA synthesizer. Commercial suppliers of synthetic polynucleotides and reagents for in vitro synthesis are well known. Methods for in vitro synthesis also include, for instance, in vitro transcription using a circular or linear expression vector in a cell free system. Expression vectors can also be used to produce a polynucleotide of the present invention in a cell, and the polynucleotide may then be isolated from the cell. Polynucleotides of the present invention may be screened by suitable methods in the art. For example, polynucleotides can be screened and identified from a random polynucleotide library by SELEX.

In one embodiment, a polynucleotide of the present invention also includes a component attached to the polynucleotide. Such a component is referred to herein as a tail. In one embodiment, a tail may be attached to the 5' end of the polynucleotide. In one embodiment, a tail may be attached to the 3' end of the polynucleotide. In one embodiment, a tail may be attached to one or more of the internal nucleotides of the polynucleotide. In one embodiment, a tail can permit a polynucleotide disclosed herein to interact with other molecules. For instance, the tail can anchor a polynucleotide of the present invention to a surface, to another molecule, or can permit a polynucleotide of the present invention to self-assemble into larger structures. The interaction mediated by the tail can be non-specific or specific. A tail can include a biodegradable component, can be entirely biodegradable, or can be non-biodegradable. A tail may be attached to the polynucleotide by a non-covalent bond, for instance, an ionic bond, a hydrogen bond, a Van der Waals force, or a combination thereof, or the attachment may be covalent. In one embodiment, more than one tail may be attached to the polynucleotide. Methods for attaching compounds to a polynucleotide are routine and known in the art.

In one embodiment, the tail can be a group allowing a specific interaction between the tail and another molecule. For instance, the tail can include a cysteine residue at the end, which mediates the binding of a polynucleotide of the present invention to gold molecules present on a surface. In another example, the tail can include an affinity label such as a biotin or an avidin/streptavidin molecule, which mediates the binding of a polynucleotide of the present invention to avidin/streptavidin or to biotin, respectively, present on a surface. Other molecules useful to bind a polynucleotide of the present invention to a surface are well known and readily available. Use of a tail allowing a specific or nonspecific interaction between the tail and another molecule permits a polynucleotide of the present invention to coat any surface or to be in the interior of any substrate, both natural and synthetic, such as glass, hydrophobic substrates, hydrophilic substrates (such as a hydrogel) or a scaffold of, for instance, non-woven mesh, foam, hydrogel, gel, or sponge. In one embodiment a 3-dimensional structure includes two or more non-contiguous surfaces, and a polynucleotide of the present invention may be present on one or more of such surfaces.

In another embodiment, the tail can be a group allowing a polynucleotide of the present invention to interact non-specifically with other molecules, including itself. For instance, the tail can be a hydrophilic group, often referred to in the art as a hydrophilic polymer. Examples of hydrophilic molecules include but are not limited to polyethylene glycol (PEG), polypropylene glycol (PPG), polyoxyethylene (POE), polyethylene oxide (PEO), polytrimethylene glycol, polylactic acid and its derivatives, polyacrylic acid and its derivatives, polyamino acid, polyoxazolidine, polyurethane, polyphosphazene, poly(L-lysine), polyalkylene oxide (PAO), polysaccharide, dextran, polyvinyl pyrrolidone, polyvinyl alcohol (PVA), polyacrylamide, and other polymers. Examples of polymers include homopolymers and heteropolymers (such as copolymers, terpolymers, tetrapolymers, etc.), and may be random, alternating, block, star block, segmented copolymers, dendrimers, or combinations thereof. Hydrophilic molecules are often useful for making scaffolds, such as hydrogels, and use of a compound containing a hydrophilic molecule attached to the polynucleotide of the present invention can result in a scaffold covered with the polynucleotide, or having the polynucleotide inside the structure.

Another type of group allowing a polynucleotide of the present invention to interact non-specifically with other molecules, including itself, is a hydrophobic molecule. The use of a hydrophobic molecule as a tail results in an amphiphile when bound to a hydrophilic polynucleotide of the present invention. An amphiphile is a compound with a hydrophobic domain and a hydrophilic domain. A hydrophobic molecule useful as a tail can be any molecule having at least one organic group (preferably, a linear chain) that is capable of forming lipid-like structures. For instance, the organic group may be an alkyl (i.e., saturated), and optionally may be unsaturated (e.g., contain at least one alkyne, at least one alkene, or a combination thereof). The organic group may be a dialkyl, and optionally one or both chains may be unsaturated, or may be a trialkyl. If unsaturated, the organic group may be polymerizable. Suitable hydrophobic molecules can be derived from compounds such as, for example, alcohols (for example, hexadecanol or octadecanol), dialkylamines, dialkylesters, and phospholipids. Examples of naturally occurring compounds from which such hydrophobic molecules can be derived include fatty acids, fatty alcohols, cholesterol, monoglycerides, diglycerides, phospholipids, cephalins, glycolipids, cerebrosides, cardiolipin, and sphingomyelin. In one embodiment, a hydrophobic molecule has one or two $C_{10}$-$C_{22}$ chains, where each chain may be saturated or unsaturated. For instance, the hydrophobic molecule may have one or two $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ chains. In one embodiment, hydrophobic molecules are useful for making a surface hydrophobic, and use of a polynucleotide of the present invention containing a hydrophobic molecule attached to the polynucleotide can result, for example, in a membrane, vesicle, or nanofiber covered with the polynucleotide.

Another type of tail that can be used is an amphiphile. Typically, the polynucleotide is attached to a hydrophilic domain of the amphiphile. Various amphiphiles are well known in the art and used routinely. The use of a hydrophobic molecule as a tail to make an amphiphile, and the use of an amphiphile as a tail, often permits self-assembly, and thus permits the production of, for instance, fibers, including nanofibers (see, for instance, Stupp and Iyer, U.S. Pat. No. 5,932,539, and Hartgerink et al., Proc. Natl. Acad. Sci. USA, 2002, 99:5133-5138), membranes, and vesicles such as liposomes, micelles, and polymersomes (see, for instance, Discher et al., U.S. Patent Publication 20050048110).

A tail, such as a hydrophobic chain (or chains), may be attached to the polynucleotide or spacer through a tail linker. Examples of linkers for use in attaching a compound, such as a dialkyl tail, to a polynucleotide having fractalkine binding activity are routinely used in the art, and include, for instance, a trifunctional amino acid, such as glutamic acid or aspartic acid. Other examples of linkers include, but are not limited to, glycerol, sphingosine, trimethylammonium-propane, dimethylammonium-propane, carnitine, ethylene glycol, 2-amino-1,3-propanediol and ortho esters.

In one embodiment, a tail also includes a structure referred to as a spacer. This structure is typically present between the tail and the polynucleotide. Thus, a compound can have the structure tail-spacer-polynucleotide, where the spacer is considered to be part of the tail or the polynucleotide, or can have the structure tail-spacer-spacer-polynucleotide, where one spacer is considered to be part of the tail and the other spacer is considered to be part of the polynucleotide. Whether a spacer is considered to be part of a polynucleotide or a tail is not intended to be limiting in any way, and merely reflects whether the spacer was produced with the polynucleotide or with the tail. A spacer is nearly any structure that is present between the tail and the polynucleotide and acts to move the polynucleotide further from the tail. A spacer may also function to provide greater flexibility of the polynucleotide with respect to the tail.

A spacer may be, for instance, amino acids, polynucleotides, polycarbons, or an organic group. A spacer can be hydrophilic or hydrophobic, can have a positive charge, negative charge, can be neutral, or a combination thereof. In some aspects, a spacer may include one or more cysteine residues, which when oxidized may form disulfide bonds to polymerize a self-assembled structure. In one embodiment, a spacer may include a hydrophilic molecule as described above. In one embodiment, a hydrophilic molecule may be a polyether, such as polyethylene glycol (PEG). A PEG monomer is $(CH_2CH_2O)_n$, and a PEG molecule present as a spacer may have, for instance, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 monomers. In one embodiment, a spacer may include a hydrophilic molecule as described above. A spacer may increase the affinity of a polynucleotide such as SEQ ID NO:1 or SEQ ID NO:2 for fractalkine. In one embodiment, a hydrophobic molecule may be an organic group such as an alkyl of $C_4$-$C_{40}$, and optionally may include at least one alkyne, at least one alkene, or a combination thereof. For instance, the organic group may be $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, or $C_{28}$ chains. In one embodiment, a spacer may include one or more nucleotides.

In one embodiment, a spacer may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 nucleotides. In one embodiment, a spacer may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides. The sequence of the nucleotide spacer is not limiting, and in one embodiment is chosen to minimize the ability to base pair with the aptamer and/or fowl secondary structure. In one embodiment, a spacer may any nucleotide. In one embodiment, a spacer may be all adenine nucleotides, all thymidine nucleotides, all guanine nucleotides, or all cytosine nucleotides.

In one embodiment, a component attached to the 5' end, the 3' end, or one or more internal nucleotides of a polynucleotide of the present invention includes a compound such as, for instance, an organic compound, an inorganic compound, a metal ion, a polypeptide, a non-ribosomal polypeptide, a polyketide, a peptidomimetic, or a polynucleotide. In one embodiment, examples of compounds include, for instance, positive or negative contrast agents that can be used for imaging such as gadolinium or magnetic particles, fluorescent dyes, chemoattractants, and therapeutic agents, such as chemotherapeutic agents and enzyme inhibitors. A compound may be therapeutic (i.e., able to treat or prevent a disease) or non-therapeutic (i.e., not directed to the treatment or prevention of a disease). In one embodiment, a compound may be a polynucleotide. Such a compound may increase the affinity of a polynucleotide such as SEQ ID NO:1 or SEQ ID NO:2 for fractalkine. In one embodiment, a polynucleotide bound to a polynucleotide such as SEQ ID NO:1 or SEQ ID NO:2 may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 nucleotides. In one embodiment, a polynucleotide compounds may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides. The sequence of the polynucleotide compound is not limiting, and in one embodiment is chosen to minimize the ability to base pair with the aptamer and/or form secondary structure. In one embodiment, a polynucleotide compound may be any nucleotide sequence. In one embodiment, a spacer may be all adenine nucleotides, all thymidine nucleotides, all guanine nucleotides, or all cytosine nucleotides.

The present invention also provides compositions that include one or more of the polynucleotides described herein. In one embodiment, a composition includes a pharmaceutically acceptable carrier. As used herein "pharmaceutically acceptable carrier" includes, but is not limited to, saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. A formulation may be solid or liquid. Administration may be systemic or local. In some aspects local administration may have advantages for site-specific, targeted disease management.

Examples of routes of administration include parenteral (e.g., intravenous, intradermal, subcutaneous, intraperitoneal, intramuscular), enteral (e.g., oral), and topical (e.g., epicutaneous, inhalational, transmucosal) administration. Appropriate dosage forms for enteral administration of the compound of the present invention may include tablets, capsules or liquids. Appropriate dosage forms for parenteral administration may include intravenous administration. Appropriate dosage forms for topical administration may include nasal sprays, metered dose inhalers, dry-powder inhalers or by nebulization.

Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline. A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of injectable compositions may be brought about by including in the composition an agent which delays absorption, for example, aluminum monostearate and gelatin.

Sterile solutions can be prepared by incorporating the active compound (e.g., a polynucleotide described herein) in the required amount in an appropriate solvent with one or a combination of ingredients such as those enumerated above, as required, followed by filtered sterilization. Generally, dispersions are prepared by incorporating the active compound into a sterile vehicle, which contains a dispersion medium and other ingredients such as from those enumerated above. In the case of sterile powders for the preparation of sterile injectable solutions, methods of preparation that may be used include vacuum drying and freeze-drying which yields a powder of the active ingredient plus any additional desired ingredient from a previously sterile-filtered solution thereof.

Oral compositions may include an inert diluent or an edible carrier. For the purpose of oral therapeutic administration, the active compound can be incorporated with excipients and used in the form of tablets, troches, or capsules. Oral compositions can also be prepared using a fluid carrier. Pharmaceutically compatible binding agents can be included as part of the composition. The tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active compounds may be delivered in the form of an aerosol spray, a nebulizer, or an inhaler, such as a nasal spray, metered dose inhaler, or dry-powder inhaler.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds may be formulated into ointments, salves, gels, or creams as generally known in the art. An example of transdermal administration includes iontophoretic delivery to the dermis or to other relevant tissues.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially. Suspensions including vesicles may also be used as pharmaceutically acceptable carriers. These can be prepared according to methods known to those skilled in the art. Vesicles are described below.

Toxicity and therapeutic efficacy of such active compounds can be determined by standard pharmaceutical procedures in cell cultures or experimental animals, e.g., for determining the $ED_{50}$ (the dose therapeutically effective in 50% of the population).

The data obtained from cell culture assays and animal studies can be used in formulating a range of dosage for use in humans. The dosage of such active compounds lies preferably within a range of concentrations that include the $ED_{50}$ with little or no toxicity. The dosage may vary within this range depending upon the dosage form employed and the route of administration used. For an active compound used in the methods of the invention, it may be possible to estimate the therapeutically effective dose initially from cell culture assays. A dose may be formulated in animal models to achieve a concentration range that includes the $IC_{50}$ (i.e., the concentration of the test compound which achieves a half-maximal inhibition of signs and/or symptoms) as determined in cell culture. Such information can be used to more accurately determine useful doses in humans.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polynucleotide or a polypeptide can include a single treatment or can include a series of treatments.

In one embodiment, a composition includes a polynucleotide of the present invention and a surface, where the polynucleotide is attached to the surface. The attachment may be non-covalent, for instance, an ionic bond, a hydrogen bond, a Van der Waals force, or a combination thereof, or the attachment may be covalent. For example, a polynucleotide can include a biotin molecule and be attached to a surface that includes avidin, or a polynucleotide can include a polymer tail that interacts non-specifically with other polymers present on a surface. In one embodiment, the composition includes a polynucleotide of the present invention present in an aqueous solution and not bound to a surface A surface can be 2-dimensional, such as a glass coverslip, a Langmuir-Blodgett membrane, or a plastic well in a tissue culture dish, or a surface can be part of a 3-dimensional structure. Examples of such structures include, but are not limited to, vesicles, such as liposomes, polymersomes, and micelles. A vesicle may include lipids, polymers, or a combination thereof. Other examples of such structures include, but are not limited to particles, such as nanoparticles (including gold nanoparticles and iron oxide nanoparticles), microparticles, dendrimer-encapsulated nanoparticles, polymeric nanoparticles, and quantum dots. Particles may optionally be solid and not include a compartment. Examples of such structures include, but are not limited to, structures that can be used to promote cell adhesion and proliferation, such as supports for 3-dimensional tissue formation. A surface may be porous and have an adequate pore size to permit the migration of cells into the structure. A surface may have varied shapes such as, for example, a tubular or cylindrical shape. Three-dimensional structures are often referred to in the art as scaffolds. The present invention also includes such surfaces, including scaffolds.

In one embodiment, the composition may include a polynucleotide of the present invention attached to the surface of a 3-dimensional structure, such as a vesicle. Examples of vesicles include, but are not limited to, liposomes, polymersomes, and particles, such as nanoparticles and microparticles. In one embodiment, a polynucleotide of the present invention may be attached to the surface of an interior compartment. Vesicles may include a lipid layer, a compartment surrounded by the lipid layer, and a polynucleotide of the present invention attached to the exterior surface of the vesicle. A polynucleotide of the present invention may be attached to the interior surface a vesicle as well. The lipid layer may be a bilayer. A polynucleotide of the present invention may be present on the surface of a vesicle by being attached to a hydrophobic molecule, e.g., a tail, that is part of the lipid layer. In one embodiment, the amount of aptamer present on the surface of a 3-dimensional structure such as a vesicle is at least 0.01 mol %, at least 0.02 mol %, at least 0.04 mol %, at least 0.06 mol %, at least 0.08 mol %, at least 0.1 mol %, at least 0.12 mol %, at least 0.14 mol %, at least 0.16 mol %, at least 0.3 mol %, at least 0.5 mol %, at least 1 mol %, at least 1.5 mol %, or at least 2 mol %. In one embodiment, the amount of aptamer present on the surface of a vesicle is no greater than 2 mol %, no greater than 1.5 mol %, no greater than 1 mol %, no greater than 0.5 mol %, no greater than 0.3 mol %, no greater than 0.18 mol %, no greater than 0.16 mol %, no greater than 0.14 mol %, no greater than 0.12 mol %, no greater than 0.1 mol %, no greater than 0.08 mol %, no greater than 0.06 mol %, or no greater than 0.04 mol %. In one embodiment, a 3-dimensional structure, such as a vesicle, having the aptamer present on its surface binds a cell having a fractalkine receptor. Methods for determining whether a vesicle binds to a cell having a fractalkine receptor are routine and known in the art, and an example of one is disclosed in Example 2. The present invention also includes such 3-dimensional structures, including vesicles, such as liposomes, polymersomes, and particles.

Vesicles useful herein may be polymerized, non-polymerized, or hybrid. Polymerized vesicles include polymerizable organic groups (for instance, an unsaturated linear chain) that can be covalently bound to other organic groups having the same or similar structure, and some, most, or all of the polymerizable organic groups are covalently bound to each other by intermolecular-interactions. Non-polymerized vesicles include organic groups that are not covalently bound to other organic groups in the lipid layer, and hybrid vesicles include domains of polymerized organic groups and non-polymerized organic groups.

Vesicles may include a variety of organic groups. In one embodiment the vesicles, such as liposomes, include at least one phospholipid, typically egg phosphatidylcholine, egg phosphatidylglycerol, distearoylphosphatidylcholine, distearoylphosphatidylglycerol, dipalmitoylphosphatidylcholine, or combinations thereof. At least one organic group present in the vesicle may be attached to the polynucleotide of the present invention, where the organic group acts as a tail. The attachment may be covalent or non-covalent.

Other phospholipids suitable for formation of vesicles that include a polynucleotide of the present invention include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphocholine (DPPC), and the like. Non-phosphorus containing organic groups may also be used in the vesicles. These include, for example, stearylamine, docecylamine, acetyl palmitate, cholesterol, fatty acid amides, and the like. Additional organic groups suitable for use in the vesicles are well known to persons of skill in the art and are cited in a variety of well known sources, e.g., McCutcheon's Detergents and Emulsifiers and McCutcheon's Functional Materials, Allured Publishing Co., Ridgewood, N.J.

The vesicles may include other components, including components that provide particular characteristics to a vesicle. The vesicles may include such components in various combinations. Vesicles may be recognized by phagocytic cells of the reticuloendothelial system, and as a result can be removed from the circulatory system and accumulate in the liver and spleen. Extended circulation times of vesicles can be promoted by inclusion of various molecules with the vesicles. For instance, small amounts (<10%) of polymerizable diacyl phosphatidyl inositol can be incorporated into vesicles, (D. Ppahadjopous et al., Liposomes: Rational Design, Janoff, A.

S. (Ed.), Marcel Dekker, New York, 1999, pp. 1-12), or polyethylene oxide (PEO) or polyethylene glycol (PEG) conjugated organic groups can be incorporated in vesicles (often referred to in the art as stealth liposomes) to achieve long circulation times (T. Ishida et al., Biosciences Reports, 2002, 22, 197-224; Woodle et al., U.S. Pat. No. 5,013,556). When PEG conjugated organic groups are used, the molecular weight of the PEG may be between at least 300 and no greater than 7000, preferably between at least 750 and no greater than 2000. A PEG molecule may be linked to an organic group by various linkages, including, for instance, a releasable linkage (Zalipsky et al., U.S. Patent Application 20060240009). Examples of useful PEG conjugated organic groups include, for instance, 1,2-Dipalmitoyl-sn-Glycero-3-Phosphoethanolamine-N-(Methoxy(Polyethylene glycol)-750)-Ammonium Salt) (PEG750) and 1,2-Dipalmitoyl-sn-Glycero-3 Phosphoethanolamine-N-(Methoxy(Polyethylene glycol)-2000)-(Ammonium Salt) (PEG-2000).

In one embodiment, the concentration of PEG present on the surface of a vesicle is the concentration that results after including at least 0.5 mol % to no greater than 20 mol % of a PEG conjugated organic group in the mixture used to make the vesicles. In one embodiment, a 3-dimensional structure, such as a polymeric nanoparticle, has a surface that is completely saturated with PEG. In one embodiment, the concentration of PEG present on the surface of a vesicle is the concentration that results after including at least 0.5 mol %, at least 1 mol %, or at least 2 mol % of a PEG conjugated organic group in the mixture used to make the vesicles. In one embodiment, the concentration of PEG present on the surface of a vesicle is the concentration that results after including no greater than 10 mol %, no greater than 9 mol %, no greater than 8 mol %, no greater than 7 mol %, no greater than 6 mol %, or no greater than 5 mol % of a PEG conjugated organic group in the mixture used to make the vesicles. Optionally, when PEG is present on the surface of a vesicle, the combined total concentration of PEG and the polynucleotide of the present invention are not so great that it results in a destabilization of the vesicle membrane. For instance, in one embodiment the combined total concentration of PEG and the polynucleotide of the present invention are not greater than 10 mol %.

Vesicles may include components that promote fusion of the vesicle with a cell membrane. For instance, fusogenic vesicles may include a hydrophobic segment extending from the surface of a vesicle for penetration into a cell membrane (Martin et al., U.S. Pat. No. 5,891,468). Other fusion-promoting molecules are well known in the art and used routinely, and include, for instance, fusion peptides that mimic portions of viruses.

Vesicles may also include components that can promote the destabilization of the vesicle lipid membrane and release of the vesicle contents when the vesicle encounters certain conditions. Such conditions include triggers such as, for instance, change in pH, mechanical stress, metal ions, temperature, ultrasound, light, alkaline phosphatase, and phospholipase $A_2$. Preferably, vesicles including a polynucleotide of the present invention are stable at physiological pH (pH 7.6 to pH 7.2, but become less stable as the pH decreases. For instance, a vesicle that is sensitive to a pH trigger can begin to release its contents when the pH of the solution surrounding the vesicle decreases to no greater than 7.0, no greater than 6.5, no greater than 6.0, or no greater than 5.5. Components that can be used to make vesicles sensitive to external triggers are well known in the art and used routinely. For example, vesicles sensitive to a pH trigger may include an organic group such as dioleoylphosphatidylethanolmaine (DOPE) (see, for instance, Simoes et al., *Adv. Drug Deliv. Rev.*, 2004; 56 (7): 947-965). Optionally, such organic groups may be stabilized in the bilayer state by inclusion of other components, for instance, cholesteryl hemisuccinate (CHEMS), or an amphipathic lipid having a bulky hydrophobic moiety, such as PEG (Zalipsky et al., U.S. Patent Application 20060240009).

Vesicles typically have a spherical structure that encapsulates an interior compartment. This interior compartment typically includes an aqueous liquid, and there may be one or more agents present in the liquid. The agent may be, for instance, a liquid, a solid that is dissolved in the liquid, a solid that is suspended in the liquid, or a lipophilic agent that stably partitions in the lipid phase of the vesicle. Examples of agents include, but are not limited to, small, water-soluble organic compounds, proteins, DNA plasmids, RNA, oligonucleotides (including antisense, siRNA, and ribozymes) and polynucleotides encoding a protein. An agent may be therapeutic (e.g., able to treat or prevent a disease) or non-therapeutic (e.g., not directed to the treatment or prevention of a disease). Examples of therapeutic agents include, for instance, chemotherapeutic agents, polypeptides, enzyme inhibitors, and oligonucleotides. Examples of non-therapeutic agents include, for instance, imaging agents for tracking progression of a disease, or for use in in vitro diagnostic assays. Imaging agents include, for example, chelates of radionuclides, iron oxide particles, fluorophores, enzymes, or fluorophores. Imaging agents may be useful for visualizing tissue through the use of MRI, PET, ultrasound imaging, fluorescent imaging, luminescent imaging, etc. In some aspects, the liquid preferably includes a pharmaceutically acceptable carrier.

Also provided herein are methods for using the polynucleotides having fractalkine binding activity. For instance, the method may include contacting a membrane with a polynucleotide of the present invention. In one embodiment, the polynucleotide may be part of a structure, where the polynucleotide attached to the surface, such as a vesicle or a particle. In one embodiment, the polynucleotide may have a component, such as a drug or an imaging agent, attached to the 5' end, the 3' end, or to one or more internal nucleotides. The membrane can be an artificial membrane (e.g., a Langmuir-Blodgett membrane), or part of a cell. The membrane may include a fractalkine polypeptide, or the chemokine domain of fractalkine, on the surface. The cell membrane can be present in conditions suitable for the internalization of the vesicle by the cell, or the contacting can be followed by exposing the cell and vesicle to conditions suitable for the internalization of the vesicle by the cell. The internalization can be active or passive. The cell is typically vertebrate, and preferably mammalian, such as human, or a member of the family Muridae (a murine animal such as rat or mouse). The cell can be ex vivo or in vivo. As used herein, the term "ex vivo" refers to a cell that has been removed from the body of a subject. Ex vivo cells include, for instance, primary cells (e.g., cells that have recently been removed from a subject and are capable of limited growth in tissue culture medium), and cultured cells (e.g., cells that are capable of extended culture in tissue culture medium). As used herein, the term "in vivo" refers to a cell that is within the body of a subject. Suitable cells are those that have fractalkine polypeptide present on their surface. Examples of readily available cells expressing fractalkine polypeptide include, for instance, activated human umbilical vein endothelial cells (HUVECs), epithelial cells, DLD-1, ECV304, ECV-CX$_3$CL1, and derivatives thereof. Cell lines may be transfected with a vector expressing a fractalkine. Primary cells such as pancreatic, gioblastoma, hepatocellular carcinoma, neuroblastoma, epithelial ovarian cancer, gastric adenocarcinoma, and colon cancer cells can be obtained from tumors. Other primary cells expressing fractalkine polypeptide include, but are not limited to, cells of the nervous system, cells of the human ovary, cells harboring HIV, and cells obtained from allograft rejection, age-related macular degeneration, atherosclerosis, rheumatoid arthritis, and allergic asthma.

When contacting a cell membrane with, for instance, a vesicle or particle includes, or is followed by, conditions suitable for the internalization of the vesicle and/or particle by the cell, the methods may be used for introducing an agent into a cell. Introducing an agent that is non-therapeutic may be used to deliver agents useful for imaging and/or diagnostic assays, thus the invention includes a method for identifying cells expressing fractalkine polypeptide, such as, for instance, tissues involved in certain cancers (e.g., pancreatic and colon cancer), HIV, allograft rejection, age-related macular degeneration, atherosclerosis, rheumatoid arthritis, pain therapy, and allergic asthma. A method for delivering agents useful for imaging and/or diagnostic assays typically include administering to a subject in need thereof a composition including an effective amount of a vesicle of the present invention, where the vesicle includes an appropriate agent. Optionally, the method further includes identifying the agent in a cell. The cell may be ex vivo or in vivo. An "effective amount" is an amount effective to elicit the desired result. In this aspect, an effective amount is the amount effective to permit the imaging or diagnosis to occur. Preferred methods for administering a vesicle of the present invention include administration by methods known in the art including, for instance, intravenous administration.

Introducing an agent that is therapeutic may be used to deliver agents useful for treating a disease, thus, the present invention also includes methods for treating certain diseases in a subject. The subject is a mammal, preferably a human. As used herein, the term "disease" refers to any deviation from or interruption of the normal structure or function of a part, organ, or system, or combination thereof, of a subject that is manifested by a characteristic symptom or set of symptoms. Diseases include, but are not limited to, cancers that include cancerous cells expressing the fractalkine polypeptide. Examples of such diseases are referred to as fractalkine polypeptide positive cancers, and include, but are not limited to, colon cancer, pancreatic cancer, neuroblastoma, epithelial ovarian cancer, and gastric adenocarcinoma. Diseases include, but are not limited to, HIV, allograft rejection, age-related macular degeneration, atherosclerosis, rheumatoid arthritis, and allergic asthma. In one embodiment disease includes chronic pain (Milligan et al. Eur J. Neurosci., 2004, 20:2294-302, Holmes et al. J. Neurochem., 2008, 106:640-9; Sun et al. Pain, 2007, 129:64-75; and Johnston et al. J. Neurosci., 2004, 24:7353-65). Typically, whether a subject has a disease, and whether a subject is responding to treatment, is determined by evaluation of symptoms associated with the disease. As used herein, the term "symptom" refers to objective evidence of a disease present in a subject. Symptoms associated with diseases referred to herein, and the evaluation of such symptoms, are routine and known in the art. Examples of symptoms of cancers include, for instance, the presence and size of tumors, and the presence and amount of biomarkers. Biomarkers are compounds, typically polypeptides, present in a subject and indicative of the progression of cancer.

Treatment of a disease can be prophylactic or, alternatively, can be initiated after the development of a disease. Treatment that is prophylactic, for instance, initiated before a subject manifests symptoms of a disease, is referred to herein as treatment of a subject that is "at risk" of developing a disease. An example of a subject that is at risk of developing a disease is a person having a risk factor, such as a genetic marker, that is associated with the disease. Treatment can be performed before, during, or after the occurrence of the diseases described herein. Treatment initiated after the development of a disease may result in decreasing the severity of the symptoms of one of the conditions, or completely removing the symptoms.

In some aspects, the methods typically include introducing into a cell an effective amount of an agent, where the agent is delivered to the cell in a vesicle and/or particle of the present invention, or the agent is attached directly to the polynucleotide. An "effective amount" in this aspect is an amount effective to decrease a symptom associated with the disease. The agent can be any therapeutic agent, and many such agents are well known and used routinely. It is expected that use of the vesicles described herein will be permit the use of lower levels of therapeutic agents and result in less of an impact on tissues and cells that do not include fractalkine polypeptides.

Whether a vesicle and/or particle, or a polynucleotide having an agent attached thereto, will function in the methods of the present invention to treat a disease can be evaluated using ex vivo models and animal models. Such models are known in the art and are generally accepted as representative of disease or methods of treating humans. When the cell is ex vivo, the result of delivering a therapeutic agent to a cell can be compared with the same type of cell that is not exposed to the agent. Such a cell that is not exposed to the agent is referred to as a control cell. A decrease in, for instance, survival or replication of the cell exposed to the agent indicates the agent was introduced into the cell.

The methods for treating a subject may include administering to a subject at risk for a disease or having the disease a composition including an effective amount of a polynucleotide of the present invention, for instance, a vesicle and/or particle having the polynucleotide of the present invention, where the vesicle includes an appropriate agent and where a symptom associated with the disease is decreased. Preferred methods for administering a vesicle of the present invention include administration by methods known in the art including, for instance, intravenous administration.

The present invention also includes methods for using a polynucleotide described herein as a fractalkine antagonist. For instance, the polynucleotide may be conjugated to a polymer such as polyethylene glycol, to increase the circulation time. Such a molecule is expected to interfere with the binding of ligand to fractalkine receptor $CX_3CR1$, including the cell-bound receptor and the soluble form of the receptor. This may be useful in preventing the metastasis of certain cancers such as prostate cancer and inhibiting the buildup of atherosclerotic plaques.

The present invention also includes methods for using a polynucleotide described herein as a research tool. The polynucleotide may be used as a research tool to probe the functions of fractalkine. Currently there are no small molecule fractalkine antagonists and researchers rely on antibodies, which are approximately 1000 times more expensive than the polynucleotides described herein.

The present invention also includes methods for using a polynucleotide described herein as a diagnostic tool. For instance, a polynucleotide of the present invention may be used as a diagnostic tool to test whether fractalkine is present in the blood or on biopsied tissues. Several studies have linked fractalkine expression to better cancer prognosis.

The present invention also provides kits for practicing the methods described herein. The kit includes, for instance, one or more of the vesicles or particles described herein, or components for the production of such vesicles or particles in a suitable packaging material in an amount sufficient for at least one administration. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that a polynucleotide described herein can be used in a method described herein. In addition, the packaging material contains instructions indicating how the materials within the kit are employed. As used herein, the term "package" refers to a solid matrix or material such as glass, plastic, paper, foil, and the like, capable of holding within fixed limits, for instance, a polypeptide. Thus, for example, a package can be a glass vial used to contain milligram quantities of a polypeptide. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

Example 1

Fractalkine (FKN) is a unique cell surface protein with potential as a therapeutic target because of its role in inflammatory diseases and cancer. Described herein is an aptamer, designated FKN-S2, with a dissociation constant of 3.4±0.7 nM that is specific to the chemokine domain of fractalkine.

Systematic evolution of ligands by exponential enrichment (SELEX) was performed to identify aptamer sequences with affinity for fractalkine. The SELEX is an iterative combinatorial method where the target molecule is exposed to $10^{14}$-$10^{15}$ random nucleotide sequences. The aptamers that bind the target are collected and amplified by polymerase chain reaction (PCR). The target is again exposed to the aptamers and the process repeated for 6 to 15 cycles at which point the aptamer pool is cloned and sequenced.

Recombinant human fractalkine containing the chemokine domain and the mucin-like stalk with a polyhistidine tag attached at its end was immobilized onto magnetic agarose beads. The polyhistidine tag binds reversibly to a $Ni^{2+}$ moiety on Ni-NTA magnetic agarose beads. This immobilization method is advantageous because fractalkine's orientation is physiologically consistent by exposing the chemokine domain at the interface. The reversible polyhistidine-$Ni^{2+}$ bond allows for selective elution of fractalkine-aptamer complex leaving behind non-specific binders (Murphy et al., 2003, *Nucl Acids Res*, 31:e110-e110). Immobilized fractalkine was exposed to a randomized library consisting of $6 \times 10^{14}$ nucleotide sequences for 1 hour. The beads were washed three times for 5 minutes to remove non-specific binders and to select aptamers with slow $k_{off}$ kinetics (Drolet et al., 1999, *Comb Chem High Throughput Screen*, 2:271-278). The aptamers with fast $k_{off}$ kinetics likely dissociate and are removed in the wash while the aptamers with slow off rates remain.

It was hypothesized that targeting the chemokine domain would produce the desirable characteristics of a fractalkine aptamer. The chemokine domain extends away from the cell increasing accessibility and improving ligand binding. Also, an aptamer that selectively binds to the chemokine domain would likely block $CX_3CR1$-fractalkine binding, whereas an aptamer binding other fractalkine domains, like the mucin-like stalk, may be non-specific because other proteins have similar structures. To do this, we modified the SELEX protocol to exploit the lack of secondary structure in mucin-like stalk (Fong et al., 2000, *J Biol Chem*, 275:3781-3786). Heating to 95° C. eliminated the chemokine domain structure while leaving the mucin-like stalk unaffected. When the denatured fractalkine was exposed to the aptamer pool, chemokine domain aptamers remained in the supernatant while other aptamers bound and were removed.

Figure 5:
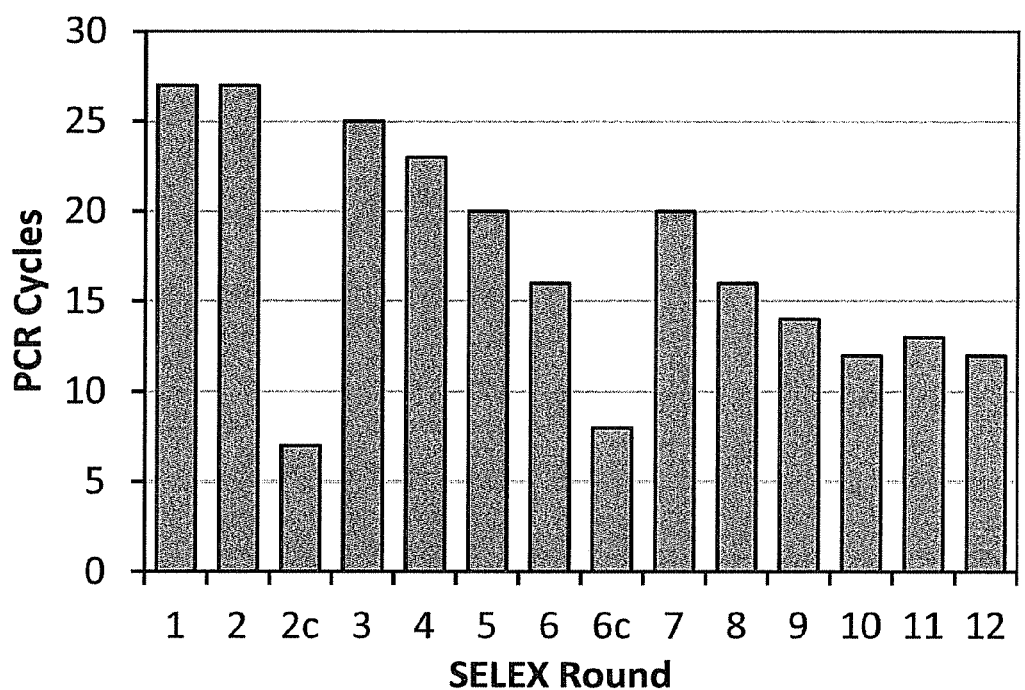
FIG. 5. The number of PCR cycles needed for aptamer pool amplification per round. The two chemokine selection steps are denoted by 2c and 6c. The chemokine domain selection steps required fewer cycles because rather can collecting the beads, only the supernatant was amplified which contained significantly more sequences.

SELEX was stopped after twelve rounds when the PCR cycles required for aptamer pool amplification leveled off indicating saturation (FIG. 5). An electrophoretic mobility shift assay (EMSA) confirmed that the aptamer pool bound fractalkine (FIG. 1). The aptamer was tagged with a biotin primer and was detected using a HRP-neutravidin chemiluminescent protocol. The aptamer bound to fractalkine (FKN) appears as a strong band in lane 2. Addition of an anti-histidine antibody (His Ab) that binds fractalkine resulted in a supershift (lane 3) due to the extra mass of the antibody. The supershift confirms the aptamer binds specifically to fractalkine. The aptamer did not bind the His Ab or bovine serum albumin (BSA) controls in lanes 4 and 5 respectively. Additionally, an anti-chemokine domain antibody (FKN Ab) blocked aptamer binding demonstrating that the aptamer binds the chemokine domain (lane 6). Additional EMSA analysis is included in FIG. 6.

After confirming the aptamer pool bound fractalkine, the pool was cloned into *E. coli* and sequenced. Of the 85 clones sequenced, approximately 95% were the same sequence differing only by single nucleotide polymerase errors. The resulting aptamer, named FKN-S2, had the sequence 5'-GGGGTGGGTG GGGGGCACGTGTGGGGGCGGC-CAGGGTGCT (SEQ ID NO:1).

Figure 2:
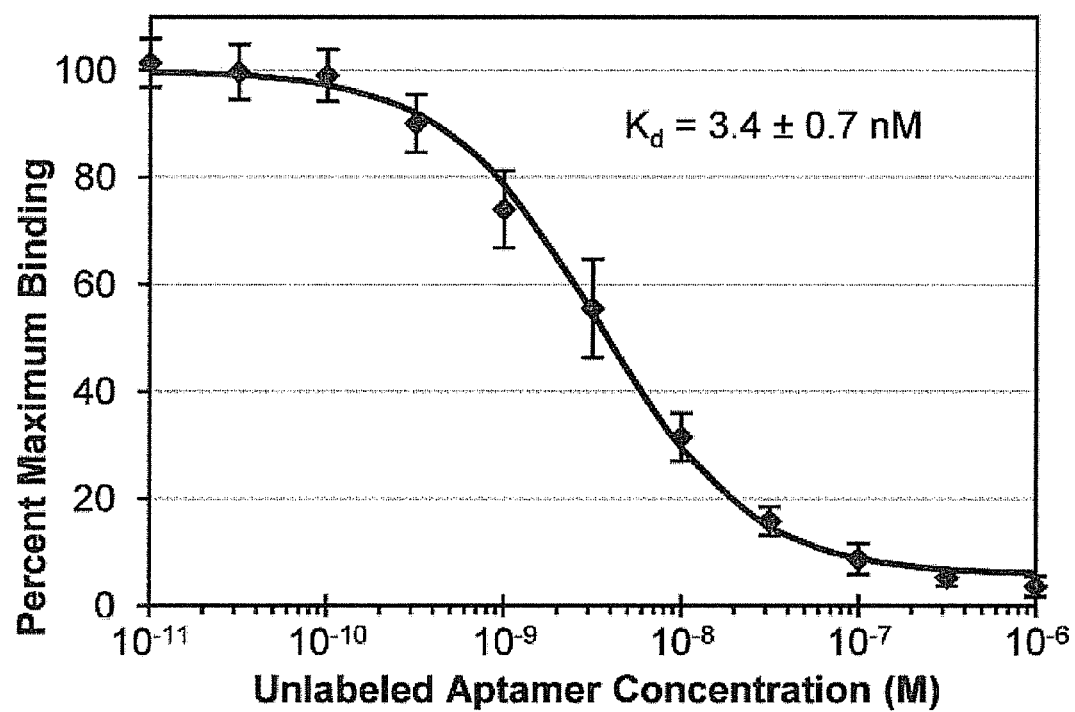
FIG. 2. Homologous competition curve for FKN-S2. Labeled and un-labeled aptamer were incubated with 25 pM of fractalkine for 1 hour. Bound aptamer was collected by filtering through a nitrocellulose membrane. Results show the mean±standard error from 9 independent experiments (n=9) with each experiment performed in quadruplicate.

The dissociation constant of FKN-S2 for fractalkine was determined using a radioactive homologous competition filter binding assay. Dilutions of unlabeled FKN-S2 aptamer were mixed with a constant concentration of $^{32}P$ ATP labeled FKN-S2. The dilutions were then incubated with 25 pM fractalkine for 1 hour at room temperature. The fractalkine concentration was iteratively decreased until it was approximately 100 times lower than the dissociation constant to prevent radioligand depletion effects. Bound aptamer was collected by filtration through a nitrocellulose membrane and the dissociation constant determined by non-linear regression analysis. The dissociation constant was determined to be 3.4±0.7 nM based on the binding curve shown in FIG. 2.

Figure 3:
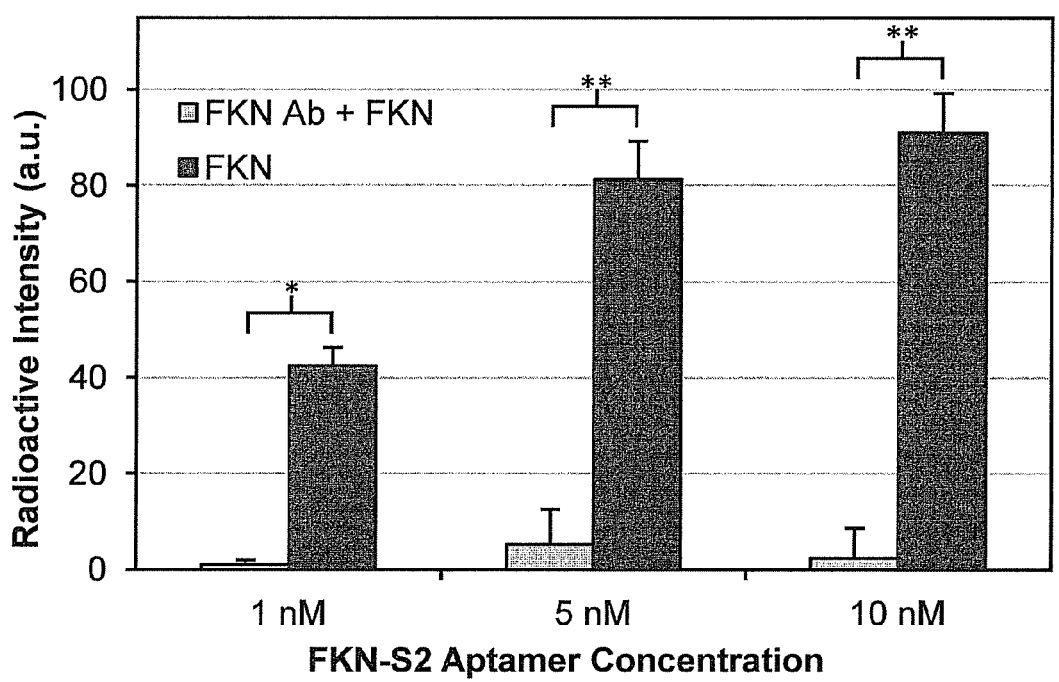
FIG. 3. Anti-fractalkine antibody blocks binding of the FKN-S2 aptamer to fractalkine. 100 nM of antibody (FKN Ab) that is specific for the chemokine domain of fractalkine was allowed to bind for 30 minutes prior to aptamer addition. Results show the mean±standard error from 4 independent experiments (n=4). Two tailed t-test with unequal variances was used to determine significance, * p<0.005, ** p<0.001.
Figure 7:
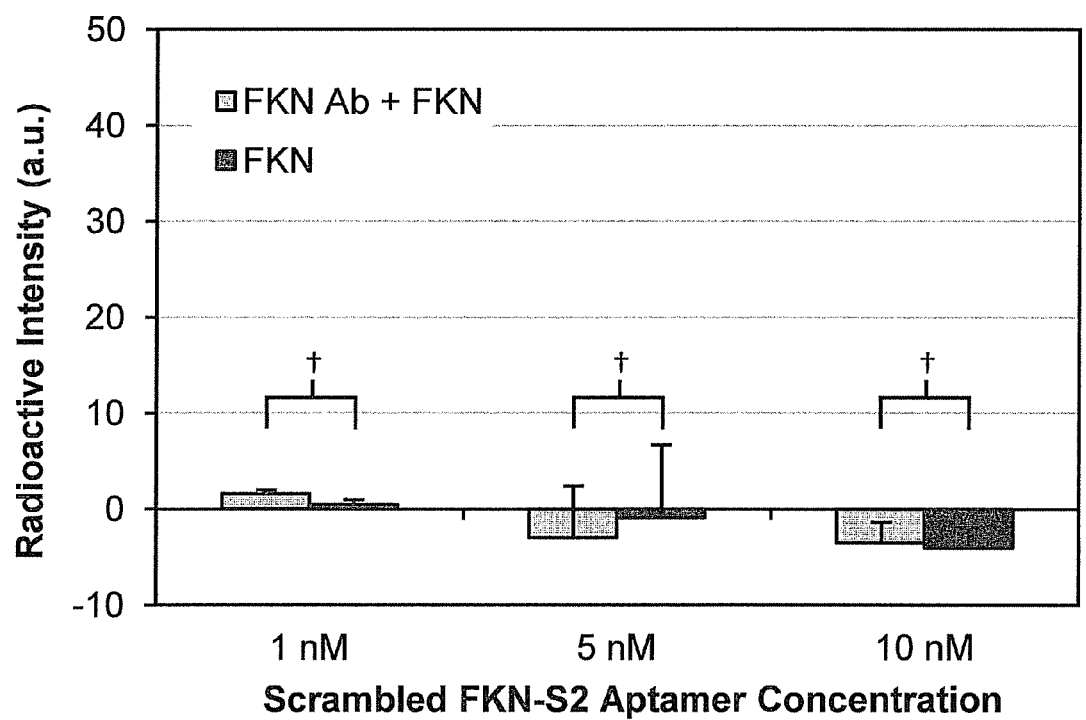
FIG. 7. Anti-fractalkine antibody blocking of binding of the scrambled FKN-S2 aptamer to fractalkine. No binding was seen for the scrambled aptamer. 100 nM of antibody that is specific for the chemokine domain of fractalkine (FKN Ab) was allowed to bind for 30 minutes prior to aptamer addition. Results show the mean±standard error from 4 independent experiments (n=4). Two tailed t-test with unequal variances was used to determine significance, †p>0.01.

EMSA analysis of the aptamer pool demonstrated the aptamer bound the chemokine domain of fractalkine. However, the synthesized aptamer was significantly different from the aptamer pool due to the removal of the flanking primer sequences and because the aptamer pool contained several sequences. To ensure the aptamer was specific to fractalkine, an anti-fractalkine chemokine domain antibody (FKN Ab) was used to block aptamer binding to fractalkine. Three aptamer concentrations, with a constant labeled to unlabeled ratio, were incubated with fractalkine and fractalkine plus the antibody (FIG. 3). Bound aptamer was collected on a nitrocellulose membrane. There was significant aptamer binding at all concentrations and the addition of the anti-chemokine domain antibody reduced binding to background levels. This demonstrates that the FKN-S2 aptamer binds directly to the chemokine domain as observed in the EMSA analysis. A similar experiment was done with a scrambled version of FKN-S2 and no binding was observed (FIG. 7).

Figure 8:
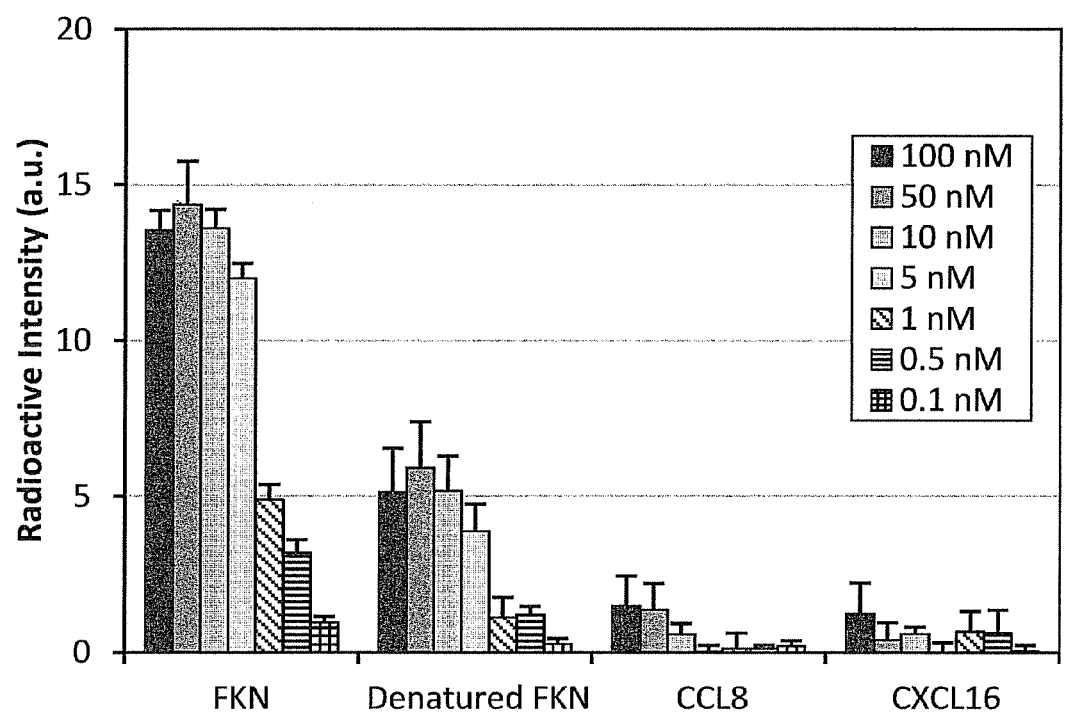
FIG. 8. FKN-S2 binding to fractalkine, heat-denatured fractalkine, chemokine CCL8 and chemokine CXCL16. The aptamer and the protein (0.2 nM) were incubated for 1 hour at room temperature. Results show the mean±standard error from five independent experiments (n=5).

To further show specificity, FKN-S2 binding was tested against fractalkine, heat-denatured fractalkine and chemokines CCL8 and CXCL16. The results are shown in FIG. 8. FKN-S2 binding to heat-denatured fractalkine was significantly reduced compared to native fractalkine while no binding was observed to either chemokines.

Figure 4:
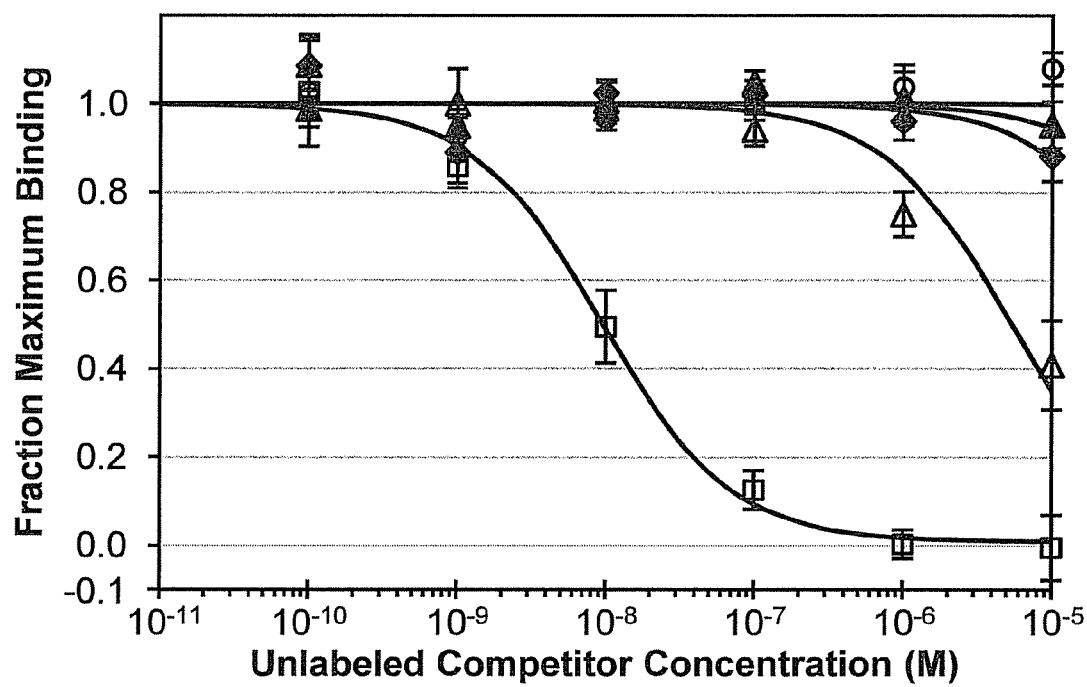
FIG. 4. Competitive binding curves of truncated FKN-S2. Open square (□) FKN-S2; Filled diamond (♦) FKN-S2a; Open triangle (Δ) FKN-S2b; Filled triangle (▲) FKN-S2c; Open circle (○) random aptamer. Results show the mean±standard error from 7 independent experiments (n=7) with each experiment performed in duplicate.

FKN-S2 contains 40 nucleotides and we investigated if truncation of the aptamer would result in sequences with similar affinity to fractalkine but with fewer nucleotides. Three truncated versions of the FKN-S2 aptamer were synthesized with five nucleotides removed from the 5' end (FKN-S2a), five from the 3' end (FKN-S2b) and five from each end (FKN-S2c). Additionally, a random 40-mer (5'-CTATCGGC-GACATGAACTTTGGCAAG GGCATCTGGTCCAT (SEQ ID NO:4)) was used as a control. The relative affinities of the truncated aptamers were tested using a heterogeneous competition assay with radiolabeled full length FKN-S2 (FIG. 4). $IC_{50}$ values (the concentration of 50% reduction in binding) were determined by non-linear regression fitting of the data to the binding equation given in herein and the values are shown in Table 1.

TABLE 1

$IC_{50}$ values of the truncated aptamers.

| | FKN-S2 | FKN-S2a | FKN-S2b | FKN-S2c | Random |
|---|---|---|---|---|---|
| $IC_{50}$ (nM) | 9.5 | 72,200 | 5,410 | >100,000 | >100,000 |

Interestingly, removal of 5 nucleotides from the 5' end (FKN-S2a) resulted in near complete loss of binding with an $IC_{50}$ value of 72,200 nM. This suggests the 5' end of the FKN-S2 aptamer is essential for binding. Removal from the 3' end (FKN-S2b) similarly gave a decrease although less drastic with an $IC_{50}$ of 5,410 nM. Sequence FKN-S2c and the random aptamer showed no binding both with $IC_{50}$ values greater than 100 μM. The large reduction in affinity after removal of 5-10 nucleotides from the FKN-S2 sequence suggest the flanking nucleotides either participate directly in binding or are essential for stabilizing the aptamer structure. The ends may directly interact with fractalkine or may create the aptamer structure necessary for binding.

In summary, we developed an aptamer via SELEX that binds with high affinity to fractalkine with a dissociation constant of 3.4±0.7 nM. The aptamer was shown to be specific for the chemokine domain of fractalkine and truncation of the aptamer significantly reducing binding. This aptamer has many potential uses including as a therapeutic agent itself, as part of a targeted drug delivery system or as an investigative tool to manipulate fractalkine-CX3CR1 binding which has shown important in different diseases such as cancer, asthma and rheumatoid arthritis.

Materials and Methods
Materials

Recombinant human fractalkine containing the chemokine domain, mucin-like stalk and a poly-histidine tag (FKN; Catalog Number 365-FR-025) and an anti-fractalkine chemokine domain antibody (FKN Ab; Catalog Number AF365) were obtained from R&D Systems (Minneapolis, Minn.). The anti-polyhistidine tag antibody was obtained from Millipore (His Ab; Billerica, Mass., Catalog Number AB3517). The aptamer library and all primers were obtained through Integrated DNA Technology, Inc. (Coralville, Iowa, USA). Ni-NTA Magnetic Agarose Beads (Catalog Number 36111) and Streptavidin MagneSphere Paramagnetic Particles (Catalog Number Z5481) were obtained from Qiagen (Valencia, Calif.) and Promega (Madison, Wis.) respectively. All PCR reagents, Hot-Start Taq DNA Polymerase (Catalog Number CB4040-1), 10×PCR buffer (Catalog Number CB3702-7) and dNTP master mix (Catalog Number CB4421-4) were obtained from Denville Scientific (South Plainfield, N.J.). The TOPO-TA cloning kit with one-shot chemically competent TOP10 *E. coli* cells (Product Number K4500-01) was obtained from Invitrogen (Carlsbad, Calif.). Chemokines CCL8 and CXCL16 were obtained from PeptroTech (Rocky Hill, N.J.).

Selection of Aptamers Against Fractalkine. The aptamer library, consisting of a 40-mer random region with flanking forward and reverse priming regions, WP-18 and WP-20 respectively, are shown below. Primer WP-20 contains a biotin tag on the 5' end to facilitate strand separation. Aptamer Library, 5'-GTGCAGTCAAAGACGTCC-N40-GACCAT-GAAGTGCGATTGCC (SEQ ID NO:5); Primer WP-18, 5'-GTGCAGTCAAAGACGTCC (SEQ ID NO:6); Primer Biotin WP-20, Biotin-5'-GGCAATCGCACTTCATGGTC-3' (SEQ ID NO:8). The fractalkine was immobilized through a polyhistidine-$Ni^{2+}$ interaction. Approximately 50 μL of Ni-NTA magnetic agarose beads were combined with 1 μg of fractalkine and incubating for 1 hour at room temperature on a rotisserie shaker. The beads were washed three times to remove un-immobilized fractalkine.

For the initial round of SELEX, 50 pmol of fractalkine was incubated with 500 pmol of aptamer library for 120 minutes on a rotisserie shaker at room temperature in selection buffer (phosphate buffered saline (PBS) with 10 mM imidazole and 0.005% (v/v) Tween-20, pH 7.4). The aptamer library was heat denatured and snap cooled in ice water to eliminate hybridization. Following incubation, the beads were quickly washed three times with selection buffer followed by three 5 minute washes. The aptamer-fractalkine complex was eluted by 2 additions of 50 μL of 250 mM imidazole in PBS. The aptamer pool was amplified using polymerase chain reaction (PCR) using 1 μM of primers WP-18 and WP-20, 800 μM total dNTP and 1.25 units of Taq per 50 μL reaction. Touchdown PCR was used to amplify the aptamer pool according to the following program: 5 minutes at 95° C., 10 cycles of 5 minutes at 95° C., 15 sec at 94° C., 15 sec at 72° C.*, and 15 sec at 72° C. with the * temperature decreased by 1° C. per cycle, followed by 15 sec at 94° C., 15 sec at 62° C., and 15 sec at 72° C. with an extension step of 1 minute at 72° C. The number of cycles used was adjusted depending on the SELEX round to prevent byproduct formation. The anti-sense strand was removed by denaturing the aptamer at 95° C. for 5 minutes followed by snap cooling in ice water and incubation for 5 minutes on ice with Streptavidin MagneSphere Paramagnetic Particles. In subsequent rounds, the aptamer pool was reduced from 500 to 100 pmol while the fractalkine was reduced from 6 pmol to 1 pmol depending on the round to increase the stringency of selection. All binding occurred for 30 minutes at room temperature in selection buffer. SELEX was stopped after the $12^{th}$ round when the PCR cycles needed for amplification of the aptamer leveled off between rounds 10 to 12 (FIG. 5).

Domain Targeted SELEX: Chemokine Domain Selection Steps. Selection of chemokine domain aptamers was performed after rounds 2 and 5. Fractalkine was denatured by heating to 95° C. for 10 minutes followed by snap cooling. The fractalkine was bound to Ni-NTA beads for 1 hour. The aptamer was added and incubated in selection buffer for 60 and 30 minutes at room temperature for counter selections following rounds 2 and 6 respectively. Unbound aptamer was collected and amplified by PCR.

EMSA Analysis of Aptamer Pool. An electrophoretic mobility shift assay (EMSA) demonstrated binding of the aptamer pool to fractalkine. Asymmetric PCR was used to create biotinylated aptamer with the following reagent concentrations: DNA Polymerase (1.25 units per 50 µL reaction), 10×PCR buffer, dNTP (total dNTP concentration of 500 µM), Biotin-WP-18 (1 µM, (WP-20 (0.01 µM), water (added to 50 µl) and SELEX round 12 aptamer template (0.1 pmol).

Varying concentrations of 5' biotinylated round 12 aptamer pool was incubated with 1 pmol of fractalkine for 30 minutes at room temperature in selection buffer. A similar procedure was used for the supershift assay. An anti-polyhistidine tag antibody, fractalkine and aptamer were incubated for 30 minutes at room temperature. For the chemokine blocking experiment, 15 pmol of anti-chemokine antibody was pre-incubated with fractalkine for 15 minutes prior to aptamer addition. After binding, the samples were run at 80V on a non-denaturing 6% polyacrylamide gel in 0.5×TBE buffer (45 mM Tris-Base, 45 mM Boric Acid, 1 mM EDTA). The samples were transferred to a nylon membrane (Pall Biodyne B) at 380 mA for 30 minutes and crosslinked by UV exposure. The membrane was developed using a LightShift Chemiluminescent EMSA Kit (Thermo Scientific; Product Number 20148) according to manufacturer's instructions.

Figure 6:
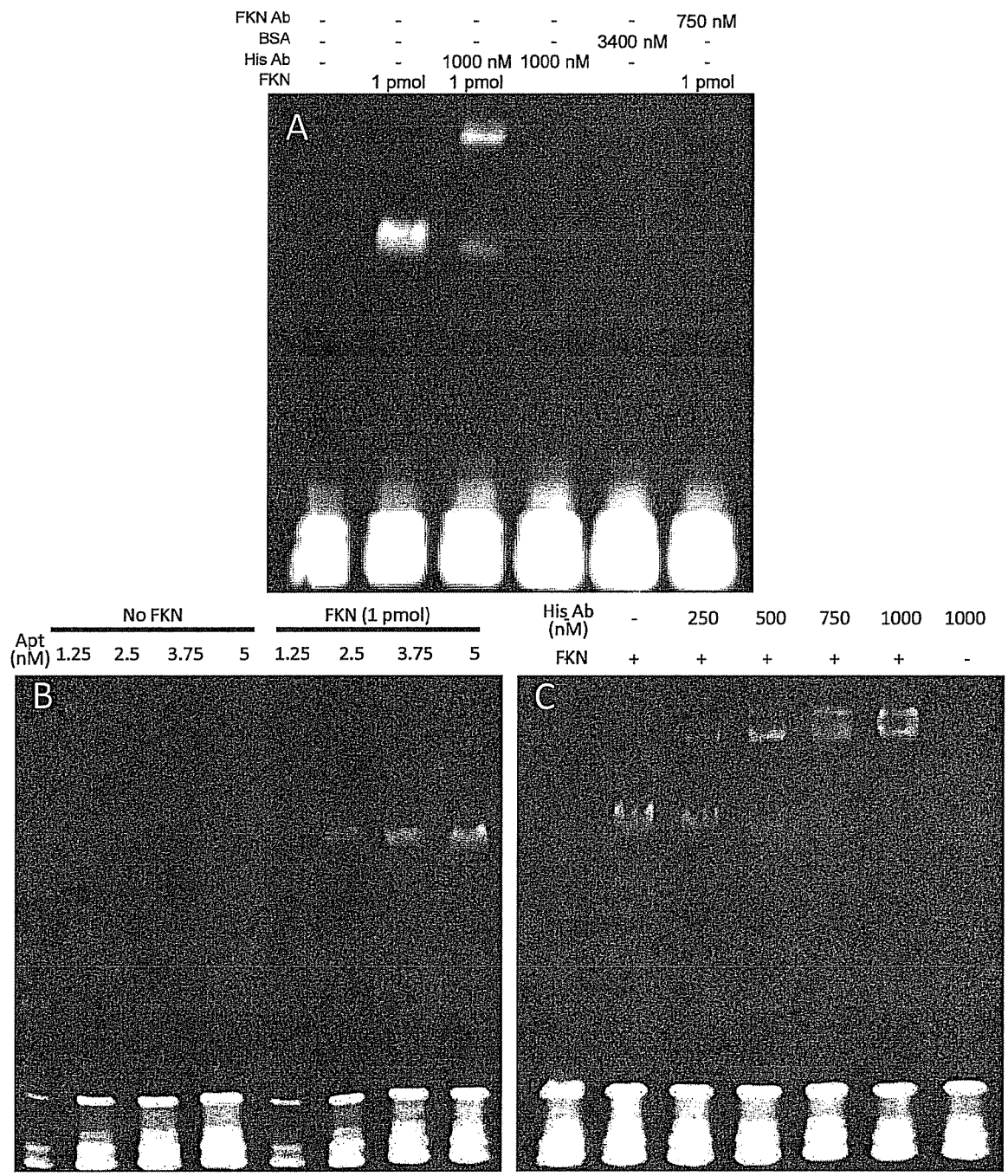
FIG. 6. (A) Full image of FIG. 1 from the main text. EMSA analysis of the 12$^{th}$ SELEX round. Lane 1: Aptamer with no FKN. Lane 2: Aptamer with FKN. Lane 3: Addition of the His Ab causes a supershift. Lane 4: The aptamer does not bind the His Ab. Lane 5: The aptamer does not bind BSA. Lane 6: An anti-chemokine domain antibody blocks aptamer binding. All lanes have 5 nM aptamer concentration. (B) Increasing concentration of SELEX aptamer pool binding to fractalkine (FKN) (C) Supershift assay with increasing concentrations of an anti-polyhistidine antibody (His Ab) showing an increased supershift corresponding to the H is Ab-fractalkine-aptamer complex. The aptamer concentration was 5 nM with 1 μmol of FKN used in each lane.

FIG. 1 is recreated in FIG. 6-A to show the entire gel which shortened for space considerations. An electrophoretic mobility shift assay confirmed that the aptamer pool bound fractalkine in a dose dependent manner (FIG. 6-B). In FIG. 6-C an increasing concentration of an anti-polyhistidine tag antibody (His Ab) bound the polyhistidine tag of the recombinant fractalkine causing a supershift of the fractalkine-aptamer band. Increasing antibody concentrations intensified the supershift while decreasing the fractalkine-aptamer band. No binding was observed in the His Ab control well indicating the aptamer does not bind the antibody.

Cloning and Sequencing of Aptamer Pool. The aptamer pool was cloned into a TA vector (Invitrogen pCR2.1 Topo TA cloning kit) and heat shocked into chemically competent *E. coli* (One Shot TOP10 Chemically Competent *E. coli*; Invitrogen) according to the manufacturer's instructions. The transformed *E. coli* were plated onto LB agar plates with 50 µg/ml kanamycin and 40 mg/mL of X-gal and successfully transformed colonies were selected through blue/white screening. The sequencing region was amplified by colony PCR and amplicon size verified by agarose gel electrophoresis. ExoSAP-IT (Affymetrix, Inc.; Product Number 78201) was used to remove the excess primers. The clones were sequenced of the M13 Forward primer on an ABI 3730xl using ABI BigDye version 3.1 terminator chemistry by the University of Minnesota BioMedical Genomic Center sequencing facility. Aptamer candidates were aligned using MEGA 5 software.

FKN-S2 Aptamer Homologous Competitive Binding Assay. FKN-S2 was labeled with $\gamma$-$^{32}$P ATP using a T4 polynucleotide kinase (PNK) (Roche Applied Science) according to the manufacturer's instructions. Briefly, 10 units of PNK were added to 25 pmol of aptamer in the supplied PNK buffer. The reaction proceeded for 45 minutes at 37° C. and was stopped by the addition of 10 µl., of a 0.5 M EDTA solution. Unincorporated $\gamma$-$^{32}$P ATP was removed using a Sephadex G-50 spin column.

The aptamer dissociation constant was measured using a homologous competitive binding assay. The aptamer concentration was quantified by UV absorbance measured using a Thermoscientific Nanodrop spectrophotometer and an extinction coefficient obtained from Integrated DNA Technology, Inc based on sequence composition.

All binding experiments occurred in binding buffer composed of PBS with 0.5 µg/mL poly dA:dT and 50 µg/mL bovine serum albumin (BSA), pH 7.4. Unlabeled full length FKN-S2 aptamer was diluted in binding buffer and a constant concentration of radiolabeled full length FKN-S2 aptamer added to each dilution. Full length fractalkine or an equivalent concentration of BSA was diluted in binding buffer to 50 pM. Aptamer and fractalkine/BSA was incubated for 1 hour at room temperature. Following incubation, samples were filtered through a nitrocellulose membrane using a bio-rad dot blot apparatus. Each well was washed 3 times with 200 µL of PBS to remove unbound aptamer. The membrane was dried and exposed to a storage phosphor screen overnight and imaged (Packard Cyclone). Binding was quantified using ImageJ and the Dot Blot Analyzer plug-in. The data was fit to the following equation $$AB = AB_{MAX}\left(\frac{[A]}{[A]+[X]+K_d}\right) - b$$

where AB is the measured signal, $AB_{Max}$ is the maximum signal, [X] is the concentration of unlabeled competitor, [A] is the hot aptamer concentration, b is the background binding, and $K_d$ is the dissociation constant. Data was fit using non-linear regression analysis with the program Origin 8.

Truncated FKN-S2 Aptamer Competitive Binding Assay. Unlabeled aptamer was serially diluted from 10,000 nM to 0.1 nM in binding buffer (PBS with 0.1 µg/mL Poly (dA:dT) and 50 µg/mL BSA, pH 7.4). 1 nM of unlabeled FKN-S2 and 5,000 cpm/µL (counts per minute/µL) of radio-labeled full length FKN-S2 were heat denatured and snap cooled before addition to either fractalkine or a BSA control at a concentration of 0.1 nM and incubated for 1 hour at room temperature. The solutions were filtered through a nitrocellulose membrane and exposed to a storage phosphor film overnight and imaged. The binding was quantified using ImageJ and the Dot Blot Analyzer plug-in. Data was fit using the non-linear regression program Origin 8 to the equation $$AB = AB_{MAX}\left(1 - \frac{[X]}{[X]+IC_{50}}\right)$$

where AB is the measured signal, $AB_{Max}$ is the maximum signal, [X] is the concentration of unlabeled competitor and $IC_{50}$ is the competitor concentration at which the signal is reduced by 50%.

Anti-fractalkine Antibody Blocking Assay. Unlabeled FKN-S2 and scrambled FKN-S2 aptamer (sequence 5'-GTTGGGATGAGGG TGGGCGGGCGCGGCGGCTGGGGGTCGG, SEQ ID NO:7) were diluted to 10 nM in binding buffer (PBS with 50 µg/mL BSA and 2.5 µg/mL Poly (dA:dT); pH 7.4). Approximately 75,000 cpm/well of radio-labeled aptamer was added and the samples were diluted to 5 and 1 nM. Each dilution was heat denatured and snap cooled. Full length fractalkine was diluted to 0.25 nM and approximately 100 nM of anti-chemokine domain antibody (FKN Ab) was added and allowed to bind for 30 minutes at room temperature. The aptamer was added to the protein solution and incubated at room temperature for 30 minutes. Bound aptamer was collected by filtering the samples thorough at nitrocellulose membrane and signal captured with a phosphor film and imaged. The background binding signal was removed from the FKN and FKN Ab+FKN samples by subtracting the signal from a well containing an identical concentration of BSA without FKN or FKN Ab. Binding was quantified using ImageJ. Results for the scrambled FKN-S2 aptamer are shown in FIG. 7.

FKN-S2 Binding to Heat-Denatured Fractalkine and Chemokines CCL8 and CXCL16. A saturation binding experiment was performed examining the binding of FKN-S2 to heat-denatured fractalkine and chemokines CCL8 and CXCL16. CCL8 represents the CC family of chemokines while CXCL16 was chosen because it is structurally similar to fractalkine. CXCL16 contains a chemokine domain atop a mucin like stock which is anchored to the cell with a transmembrane domain. The membrane bound protein is cleaved to produce a soluble version of the protein. Membrane bound CXCL16 can also act as an adhesion molecule to certain T cell types. These similarities to fractalkine made it an excellent candidate to test FKN-S2 binding.

FKN-S2 was labeled with $\gamma$-$^{32}$P ATP using a T4 polynucleotide kinase as described in the FKN-S2 Aptamer Homologous Competitive Binding Assay section. Unlabeled FKN-S2 aptamer and $10^6$ counts per minute of radiolabeled FKN-S2 aptamer were mixed in binding buffer (PBS with 50 µg/mL BSA and 2.5 µg/mL Poly (dA:dT); pH 7.4) and the aptamer was denatured at 95° C. for 5 minutes followed by snap cooling in ice water for 5 minutes. The aptamer was then serial diluted in binding buffer and the dilutions added to full length fractalkine, heat-denatured fractalkine and chemokines CCL8 (PeproTech Catalog Number 300-15) and CXCL16 (PeproTech Catalog Number 300-55). All proteins were at a concentration of 0.2 nM. Fractalkine was denatured by heating to 95° C. for 10 minutes followed by incubation on ice until use. The aptamer and protein were incubated for 1 hour at room temperature. Bound aptamer was collected by filtering the samples thorough at nitrocellulose membrane and signal captured with a phosphor film and imaged. The background was measured from wells containing an identical concentration of BSA without the protein. Binding was quantified using ImageJ. Results are shown in FIG. 8. FKN-S2 did not bind to the chemokines CCL8 or CXCL16, however, some binding was seen to heat-denatured fractalkine. Heat-denaturing reduced binding by 2.5 fold at saturation. The binding that was seen may be due to incomplete denaturing or refolding of fractalkine during the experiment.

Example 2

Methods $IC_{50}$ Binding Assay. FKN-S2 aptamer was labeled on the 5' end with a radioactive phosphorous ($^{32}$P) using a T4 kinase. Unlabeled aptamer amphiphile was serially diluted in binding buffer composed of PBS with BSA, Poly(dA:dT) and radiolabeled FKN-S2 (generally less than 0.05 nM; ≈20,000 count per minute per well) and unlabeled FKN-S2 (1 nM). This ensured each aptamer dilution contained an identical concentration of FKN-S2. Fractalkine (0.1 nM) or BSA was added to each dilution and the aptamer was allowed to bind for 1 hour at room temperature. Each solution was then filtered though a nitrocellulose membrane where the fractalkine:aptamer complex was captured and non-bound aptamer was removed by washing the membrane three times with PBS. The membrane was then exposed to a phosphor film overnight and imaged. The binding was quantified using imageJ and the data fit to a binding equation to determine the $IC_{50}$.

$$\text{Intensity} = \text{Intensity}_{Max} * \left(1 - \frac{[\text{Amphiphile}]}{[\text{Amphiphile}] + IC_{50}}\right) + b$$

Intensity is the measured radioactivity, $\text{Intensity}_{Max}$ is the intensity at an amphiphile concentration of 0 nM, [Amphiphile] is the concentration of the competitor aptamer amphiphile, $IC_{50}$ is the amphiphile concentration at which half the binding is inhibited, and b corrects for background binding. Intensity, $\text{Intensity}_{Max}$ and b are varied to minimize the error in the fit using a non-linear regression program.

Tail Synthesis. A dialkyl tail was conjugated to the aptamer to facilitate incorporation of the aptamer into the liposome. The structure of the dialkyl tail is shown in FIG. 9A and they were synthesized as described elsewhere and stored at −20° C. (Garg et al., 2009, Int. J. Pharm., 366:201-210). In order to conjugate the tails to the aptamer, the tails were activated with an N-hydroxysucinimide (NHS) group off the carboxyl group. The NHS-tail conjugate is called NHS-tails. The NHS-tails react with primary amines forming an amide bond. The tails were dissolved in dichloromethane and a 1.1 time excess of dicyclocarbodiimide and N-hydroxysucinimide were added and allowed to react overnight at 50° C. The dicyclohexylurea was removed by filtration and the dichloromethane dried off under argon. The NHS-tails were then dissolved in ethyl acetate at 50° C. and precipitated by cooling to 4° C. The precipitate was collected, dried under vacuum and stored at −20° C. Successful activation was verified by mass spectrometry.

Aptamer Amphiphile Synthesis. The aptamer was obtained from IDT DNA Technologies (Coralville, Iowa) with a six carbon amino spacer on either the 3' or 5' end. In order to dissolve the aptamer in an organic solvent, like dimethylformamide (DMF) or dimethyl sulfoxide (DMSO), it was converted into an aptamer: cetyltrimethylammonium bromide (CTAB) salt. The aptamer, 250 µM, was dissolved in water and a 1.5 times excess (based on a 1:1 CTAB:DNA phosphate ratio) of CTAB was added. The CTAB:aptamer precipitate was collected and dried under vacuum to remove all water. The CTAB:aptamer was then dissolved in DMF with 10% DMSO and 10 times excess of NHS-tails added. The mixture was reacted for 48 hours at 60° C. The DMT was removed under a stream of argon. The reaction product was dissolved in 825 µL of ethanol and 30 µL of 3M sodium acetate and 300 µL of water added to precipitate the aptamer. The sodium acetate displaces the CTAB from the aptamer and the ethanol precipitates the aptamer. The precipitate was collected by centrifugation, dissolved in water and precipitated again with sodium acetate and ethanol. The aptamer precipitate was dissolved in water and filtered to remove any particulate prior to HPLC purification. The conjugated aptamer was separated from the non-conjugated aptamer by HPLC using an Agelent Zorbax C-18 column using a water-methanol gradient with 100 mM hexafluoro-2-propanol and 15 mM triethylamine. The aptamer conjugate peak was collected, dried under argon and purified by ethanol precipitation. Aptamer with a conjugated tail is referred to as aptamer-amphiphile.

Liposome Synthesis. Liposome films were made as described previously with slight modifications (Garg et al., 2009, Int. J. Pharm., 366:201-210). The liposomes were extruded through a 200 nm diameter membrane and the unencapsulated dye and lipids were removed by dialysis in a 50,000 molecular weight cutoff membrane. The liposomes were functionalized with aptamer-amphiphile using a post insertion technique. Three micromoles of liposomes (measured by total lipid content) were incubated with varying amounts of aptamer-amphiphile at 45° C. overnight. Unincorporated aptamer-amphiphile was removed by FPLC on a sephadex CL-4B column. The amount of aptamer-amphiphile incorporated into the liposomes was quantified by precipitating the aptamer-amphiphile using an ethanol precipitation step and quantified by absorbance at 260 nm.

Confocal Microscopy. The murine colonic epithelial cell line MCA-38 (Dieleman et al., 1994, Gastroenterol., 107: 1643) was transfected to express fractalkine and designated MCA-38.FKN. Approximately $2\times10^5$ MCA-38.FKN cells were seeded onto a fibronectin coated glass cover slip and allowed to adhere overnight. 3' 10T FKN-S2 functionalized liposomes (0.16 mole % FKN-S2) were incubated with the cells for 1 hour at 37° C. at a lipid concentration of 250 uM. Following incubation, the cells were washed three times with PBS supplemented with 2% FBS and fixed by addition of 4% paraformaldahyde for 15 minutes at 37° C. The cell membrane (Invitrogen wheat germ agglutinin alexa fluor 594) and nucleolus (Invitrogen Hoechst 33342) were stained in PBS and the cells washed three times with buffer. The glass cover slips were then mounted onto glass slides using Invitrogen prolong gold antifade reagent. The slides were imaged on an Olympus FluoView 1000 BX2 Upright Confocal from the University of Minnesota University Imaging Centers.

Circular Dichroism. The aptamers were diluted to approximately 10 μM in water and the circular dichroism spectrum of each sample measured using a JASCO J-815 Spectropolarimeter from the University of Minnesota Biophysical Spectroscopy Center.

Results

Figure 9:
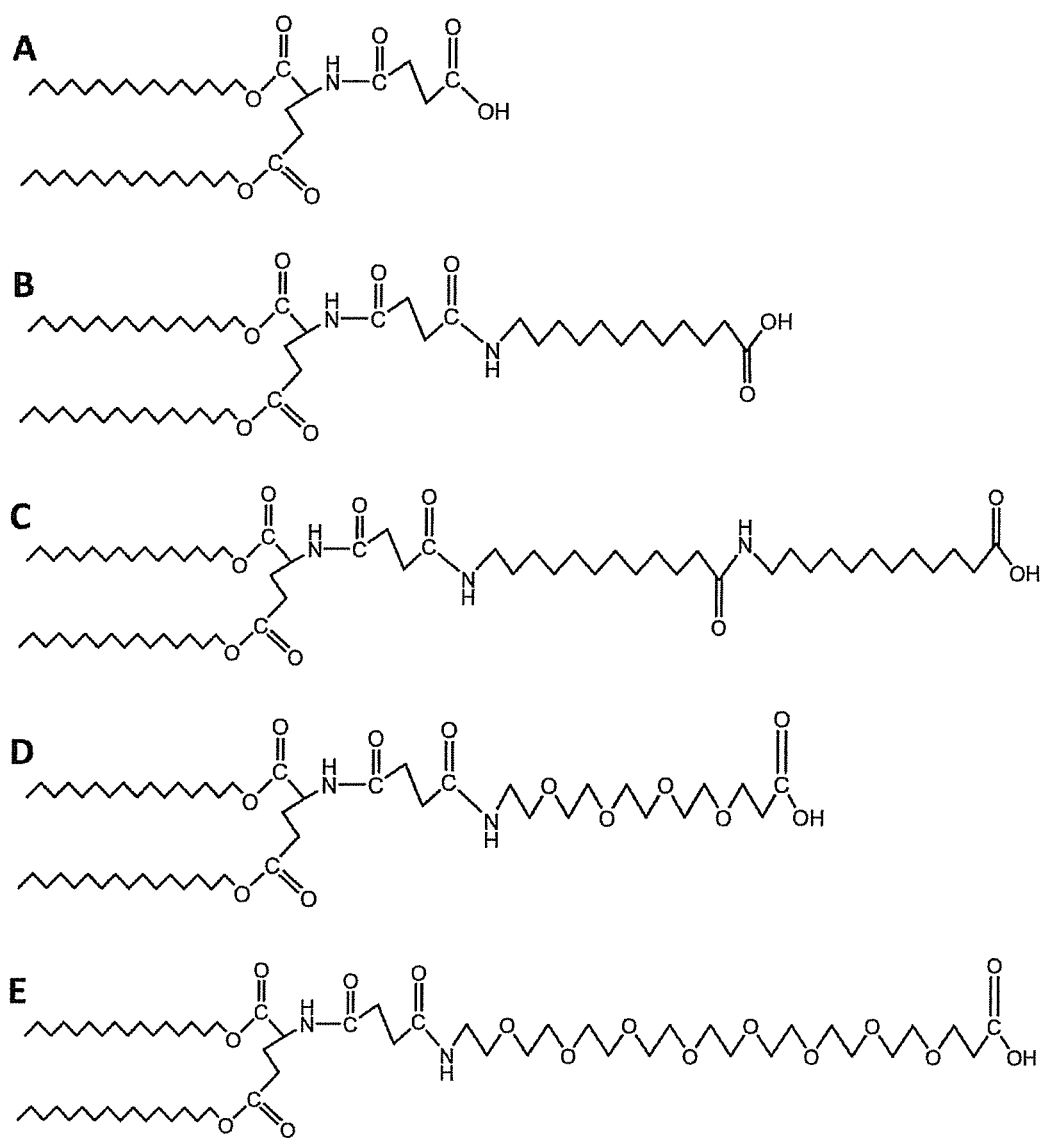
FIG. 9. Structures of dialkyl tails and spacers. A: No spacer tail. B: C12 spacer tail. C: C24 spacer tail. D: PEG4 spacer tail. E: PEG8 spacer tail. The PEG 12 and PEG24 tails are similar to the PEG4 and PEG8 spacer tails with additional PEG monomer units. The aptamer was conjugated off the terminal carboxyl group to a primary amine on the aptamer. Conjugation was performed through the NHS chemistry.
Figure 10:
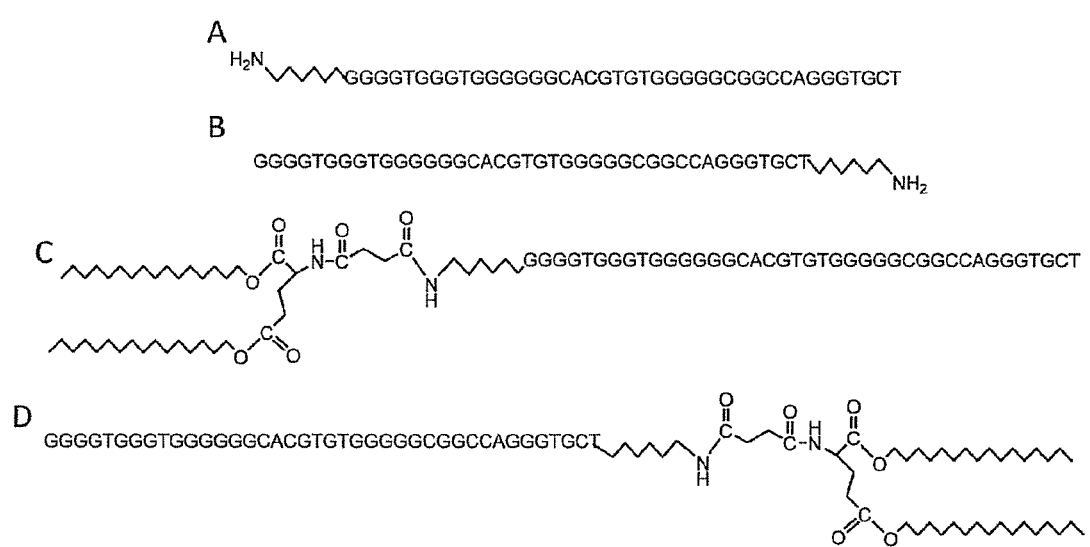
FIG. 10. A: aptamer with the C6 primary amine on the 5' end. B: Aptamer with the C6 primary amine on the 3' end. C: 5' No Spacer FKN-S2 Amphiphile. D: 3' No Spacer FKN-S2 Amphiphile. The sequence presented is SEQ ID NO: 1.

A dialkyl tail was conjugated to the aptamer to facilitate incorporation of the aptamer into liposomes. The tail was composed of two C16 alkyl chains ester bonded to glutamic acid with a carboxyl headgroup. The structure of the tail is shown in FIG. 9A. The aptamer was synthesized with a terminal amino group on either the 5' or 3' end attached to the aptamer through a C6 linker. (FIGS. 10 A and B). To make the tail amine reactive, a NHS group was added to the carboxyl group using the N-hydroxysuccinimide (NHS)/dicyclocarbodiimide (DCC) chemistry. The NHS group reacts with the amine on the aptamer forming an aptamer-amphiphile. The tail can be added to either the 5' or 3' end of the aptamer. FIGS. 10 C and D show the 5' and 3' aptamer-amphiphiles respectively. A spacer molecule can be added between the tail and the aptamer to alter the self-assembly and binding properties of the aptamer-amphiphile. The structures of different tails and spacers are shown in FIG. 9. The PEG4, PEG8, PEG12 and PEG24 spacer tails have 4, 8, 12 and 24 PEG monomer repeat units $(CH_2CH_2O)_n$ between the tail and the aptamer respectively and the C12 and C24 tails have 12 and 24 carbon molecules between the tail and the aptamer respectively.

Effect of the Spacer on Binding Affinity.

Addition of the tail significantly decreases the binding affinity of the aptamer as determined by a competitive binding assay. Radiolabeled FKN-S2 aptamer and unlabeled aptamer-amphiphile were incubated with fractalkine for 1 hour and the aptamer:fractalkine complex collected by filtration through a nitrocellulose membrane. The concentration at which 50% of the aptamer is displaced by the unlabeled competitor is the $IC_{50}$ value. The $IC_{50}$ values of the aptamer-amphiphiles are listed in Table 2. Conjugation of the tail to FKN-S2 increased the $IC_{50}$ value from 8.6±0.3 nM for the aptamer to 65.7±3.5 nM and 81.6±6.6 nM for 3' no spacer FKN-S2 amphiphile and 5' no spacer FKN-S2 amphiphile respectively.

TABLE 2

$IC_{50}$ values of aptamer amphiphiles

| Amphiphile | $IC_{50}$ (nM) | n |
|---|---|---|
| FKN-S2 | 8.6 ± 0.3 | 9 |
| 5' No Spacer FKN-S2 Amphiphile | 81.6 ± 6.6 | 6 |
| 3' No Spacer FKN-S2 Amphiphile | 65.7 ± 3.5 | 9 |
| 3' PEG4 FKN-S2 Amphiphile | 68.6 ± 7.1 | 7 |
| 3' PEG8 FKN-S2 Amphiphile | 47.5 ± 6.1 | 8 |
| 3' PEG 24 FKN-S2 Amphiphile | 49.6 ± 6.1 | 6 |
| 3' C12 FKN-S2 Amphiphile | 75.6 ± 5.6 | 6 |
| 3' C24 FKN-S2 Amphiphile | 73.5 ± 5.6 | 6 |
| 3' 5T FKN-S2 Amphiphile | 37.6 ± 0.6 | 3 |
| 3' 10T FKN-S2 Amphiphile | 21.8 ± 2.0 | 9 |
| 5' 10T FKN-S2 Amphiphile | 55.1 ± 4.9 | 3 |
| 3' 10A FKN-S2 Amphiphile | 24.8 ± 2.0 | 6 |

Aptamer orientation had a significant effect on the affinity of the aptamer-amphiphile. The affinity of the 3' no spacer FKN-S2 amphiphile was 19% greater than the 5' no spacer FKN-S2 amphiphile. All further investigations into the effect of the spacer looked only at the 3' conjugation.

The spacer also had a significant effect on binding affinity. The C12 (75.6±5.6 nM) and C24 (73.5±5.6 nM) spacers had higher $IC_{50}$ values than the no spacer amphiphile. This may be due to the hydrophobicity of the spacer. The PEG4 spacer (68.6±7.1 nM) did not improve binding affinity relative to the no spacer amphiphile. However increasing the PEG spacer length from PEG4 to PEG8 (47.5±6.1 nM) did but longer spacers, PEG24 (49.6±6.1 nM), did not further improve aptamer affinity.

Figure 11:
FIG. 11. Structure of the 3' 10T FKN-S2 aptamer-amphiphile. The sequence presented is SEQ ID NO:9.

The spacer with the highest affinity was the 3' 10T. The 10T spacer is made through the addition of 10 thymidine nucleic acids added to either the 3' or 5' end of the FKN-S2 aptamer and conjugation to a no spacer tail. FIG. 11 is a structure of the 3' 10T FKN-S2 aptamer-amphiphile. The 3' 10T FKN-S2 amphiphile had an $IC_{50}$ of 21.8±2.0 nM which is significantly lower than other aptamer-amphiphiles. Other nucleic acid spacers were tested including 3' ST (37.6±0.6 nM), 5' 10T (55.1±4.9 nM) and 3' 10A (24.8±2.0 nM). The 10A spacer is composed of adenosine nucleic acids and has a similar $IC_{50}$ as the 10T suggesting the improved affinity is not a sequence dependent effect.

We hypothesized that the improvement in affinity of the 3' 10T FKN-S2 amphiphile may be due either to a spacer effect, where the spacer increases the distance between the aptamer and the tail, or due to an improvement in the affinity of the aptamer itself. To investigate the effect of the 10T spacer on the aptamer affinity, we measured the $IC_{50}$ values of the FKN-S2 aptamer with different nucleotide spacers (Table 3). Addition of 1 thymidine base on the 3' end of FKN-S2 did not affect the affinity of the aptamer (9.2±2.3 nM) However, addition of 5T and 10T did significantly increase the FKN-S2 affinity for fractalkine with $IC_{50}$ values of 3.4±0.6 nM and 3.6±0.9 nM respectively. Addition of the 10T spacer to the 5' end did not significantly affect affinity (8.7±1.8 nM) while 10T spacers on both the 5' and 3' ends (2.7±0.3 nM) resulted in an affinity similar to that of the 3' 10T FKN-S2 aptamer. Addition of the first 10 bases of the primer sequence used to identify FKN-S2 did not result in an improvement in affinity like the 10T.

TABLE 3

IC$_{50}$ values of FKN-S2 aptamer analogs

| Aptamer | IC$_{50}$ (nM) | n |
|---|---|---|
| 3' 1T FKN-S2 Aptamer | 9.2 ± 2.3 | 6 |
| 3' 5T FKN-S2 Aptamer | 3.4 ± 0.6 | 6 |
| 3' 10T FKN-S2 Aptamer | 3.6 ± 0.9 | 6 |
| 5' 10T FKN-S2 Aptamer | 8.7 ± 1.8 | 6 |
| 5',3' 10T FKN-S2 Aptamer | 2.7 ± 0.3 | 6 |
| 3' Primer FKN-S2 Aptamer | 9.0 ± 1.4 | 6 |

Effect of Spacer on Liposome Binding.

Figure 12:
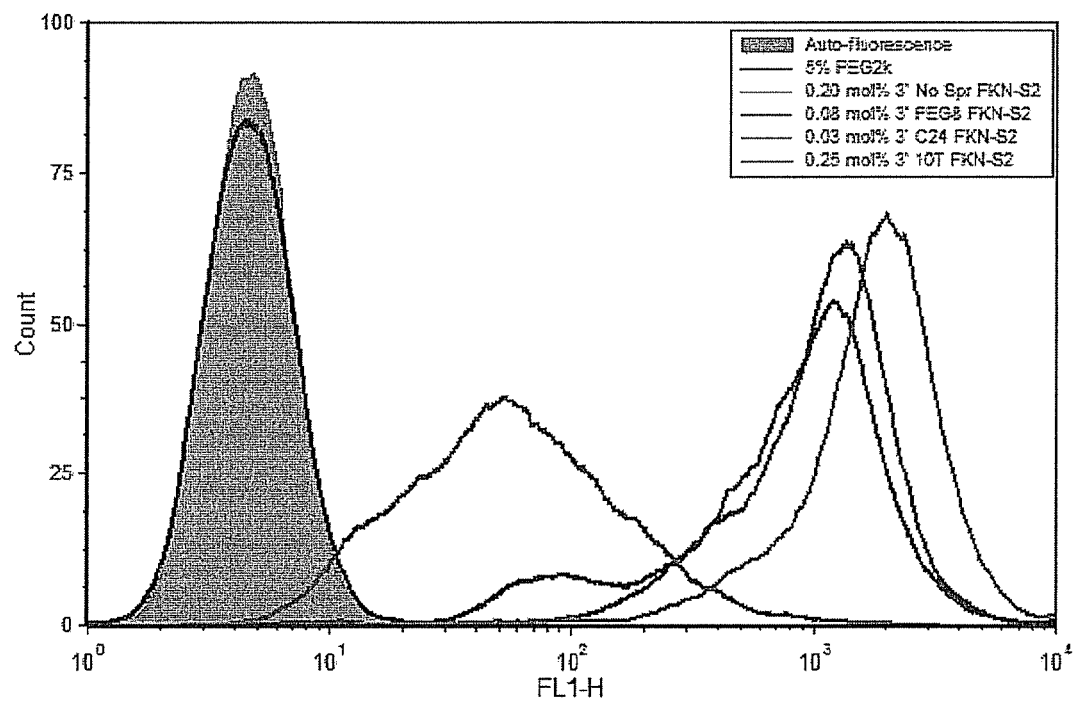
FIG. 12. Flow cytometry histogram of liposomes targeted to MCA-38.FKN cells. Four different spacers were used for the FKN-S2 aptamer amphiphiles.

Four different spacers were investigated in liposomes. All the aptamers were conjugated on the 3' end. The 3' No Spacer FKN-S2, 3' PEG 8 FKN-S2, 3' C12 FKN-S2 and 3'10T FKN-S2 aptamer amphiphiles were incorporated into 200 nm liposomes with 5% PEG 2000 loaded with 2 mM calcein. The liposomes were incubated with MCA-38.FKN colon cancer cells grown on a 12 well plate. The liposomes were incubated at a lipid concentration of 250 µM for 1 hour at 37° C. in DPBS buffer (137 mM sodium chloride, 2.7 mM potassium chloride, 8.1 mM sodium phosphate monobasic, 1.76 mM potassium phosphate dibasic, 0.91 mM calcium chloride, 0.49 mM magnesium chloride pH=7.4). The cells were detached from the plate and fluorescence quantified by flow cytometry. The flow cytometry was performed on a BD FACSCalibur system at the Flow Cytometry facility at the Masonic Cancer Center at the University of Minnesota. The flow cytometry histogram of fluorescence is show in FIG. 12.

Figure 13:
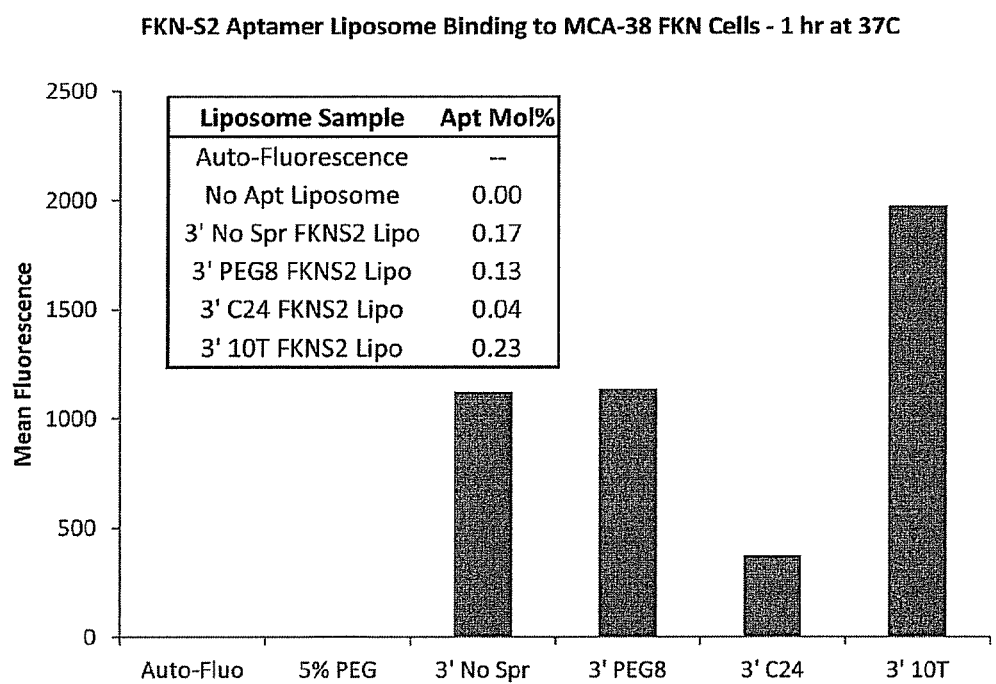
FIG. 13. Mean fluorescence of FKN-S2 aptamer liposomes as measured using flow cytometry (n=2).

This experiment was repeated for a total of n=2 and the mean fluorescence and aptamer concentration graphed in FIG. 13. The results of the flow cytometry binding experiment show that the 3' 10T FKN-S2 amphiphile liposome formulation performs significantly better than the other spacers.

Effect of Aptamer Concentration on Liposome Binding.

Figure 14:
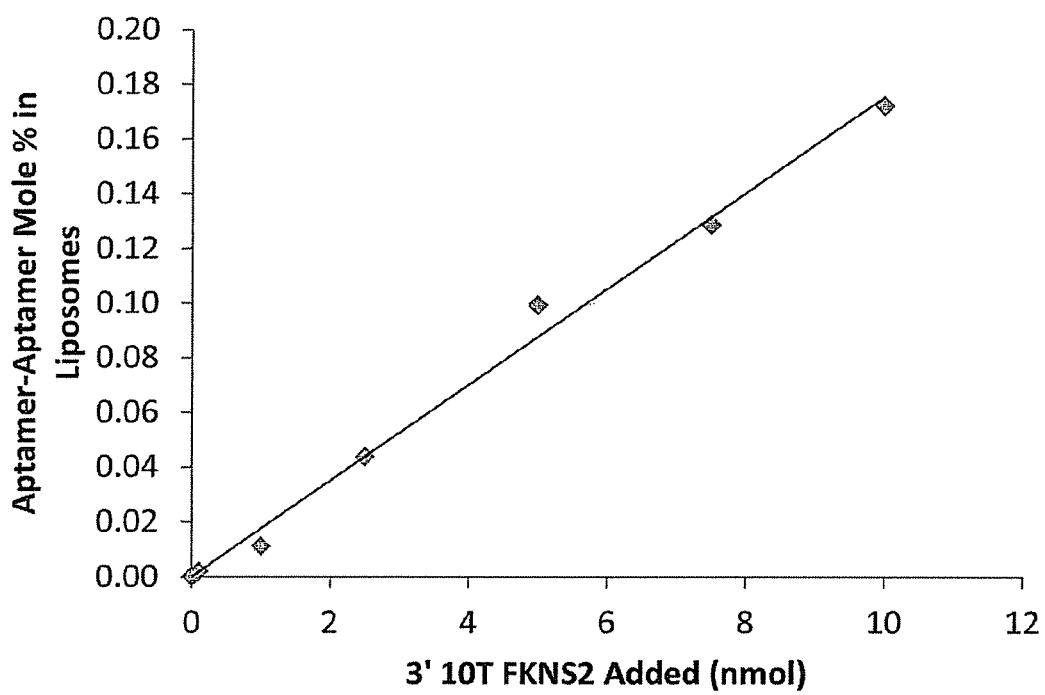
FIG. 14. Graph of the aptamer-amphiphile mole percent in liposomes verses the amount of aptamer-amphiphile added to the non-functionalized liposomes. There is a linear relationship between the amount of aptamer-amphiphile added to the amount of aptamer-amphiphile incorporated into the liposome bilayer.

The effect of aptamer concentration was investigated using the 3' 10T FKN-S2 amphiphile liposomes. Varying concentrations of the 3' 10T FKN-S2 aptamer-amphiphile were incubated overnight at 45° C. with 5% PEG2000 liposomes (200 nm diameter) loaded with 2% mM calcein. The aptamer-amphiphile inserted into the liposome bilayer functionalizing the liposomes with aptamer. Unincorporated aptamer-amphiphile was removed by FPLC. The amount of aptamer-amphiphile added to the liposomes correlated well with how much aptamer-amphiphile incorporated into the membrane as shown in FIG. 14.

Figure 15:
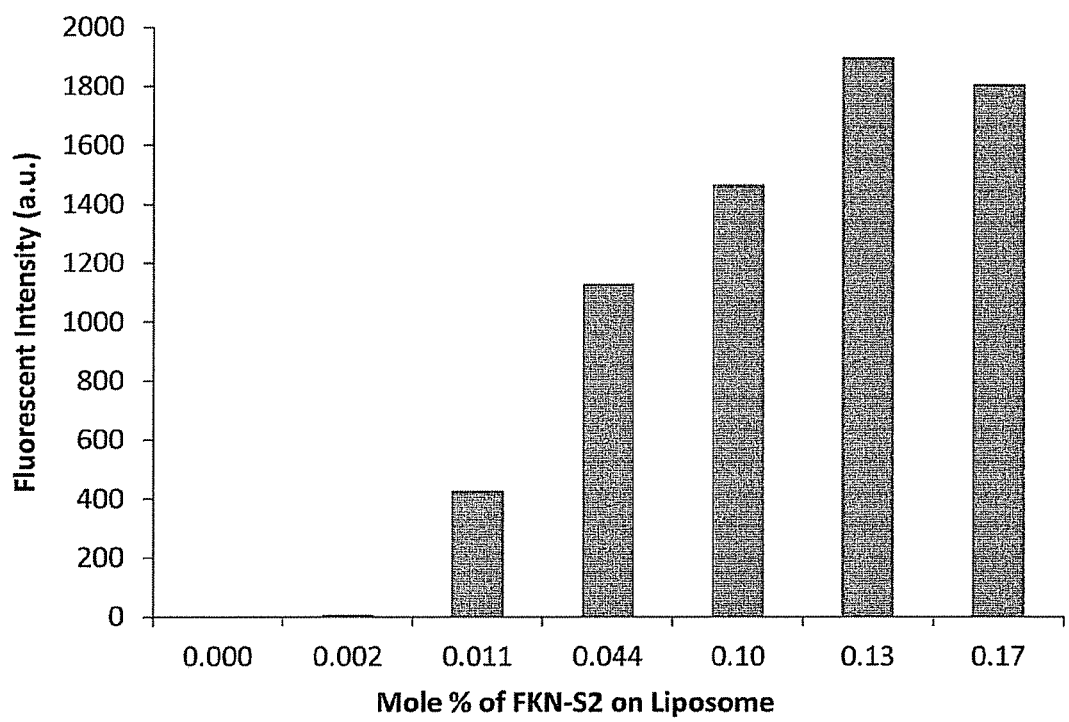
FIG. 15. Effect of 3' 10T FKN-S2 aptamer-amphiphile concentration on liposome binding. Binding was done at 37° C. for 1 hour at a liposome lipid concentration of 250 μM to MCA-38.FKN cells.

The 3' 10T FKN-S2 functionalized liposomes were incubated with MCA-38.FKN cells in a 12 well plate for 1 hour at 37° C. at a lipid concentration of 250 uM. The cells were detached from the plate and the fluorescence measured using flow cytometry. The average fluorescent intensity of two experiments is shown in FIG. 15. The results show an increase in fluorescence with increasing 3' 10T FKN-S2 amphiphile concentration until around 0.13 mole % after which the fluorescence appears to level off.

Confocal Microscopy of 3' 10T FKN-S2 Aptamer Liposomes.

Figure 16:
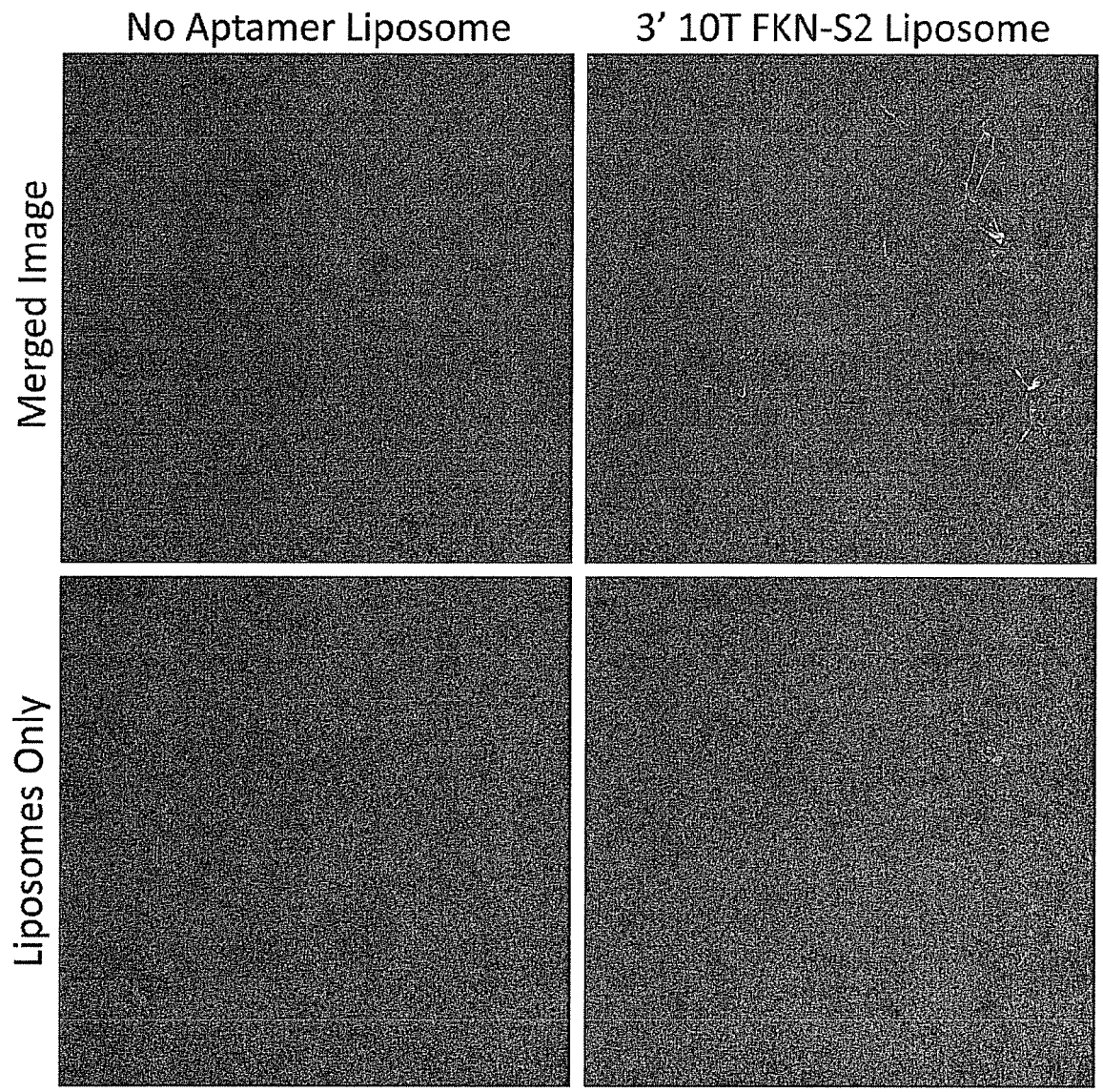
FIG. 16. Confocal images of 3' 10T FKN-S2 aptamer amphiphile liposomes targeted to MCA-38.FKN cells for 1 hour at 37° C.

To investigate binding and internalization of the 3' 10T FKN-S2 aptamer liposomes a confocal imaging experiment was performed. 3' 10T FKN-S2 aptamer liposomes (250 µM) were incubated with MCA-38.FKN cells for 1 hour at 37° C. Unbound liposomes were washed away and the cells were fixed, stained and mounted on glass slides. Confocal images of cells are shown in FIG. 16. The FKN-S2 targeted liposomes clearly show significant binding to the cells while the untargeted liposomes show little to no binding. While the majority of the liposomes are bound to the outside of the cell, there was significant internalization of the liposomes.

Circular Dichroism Spectroscopy of FKN-S2 Amphiphiles.

Figure 17:
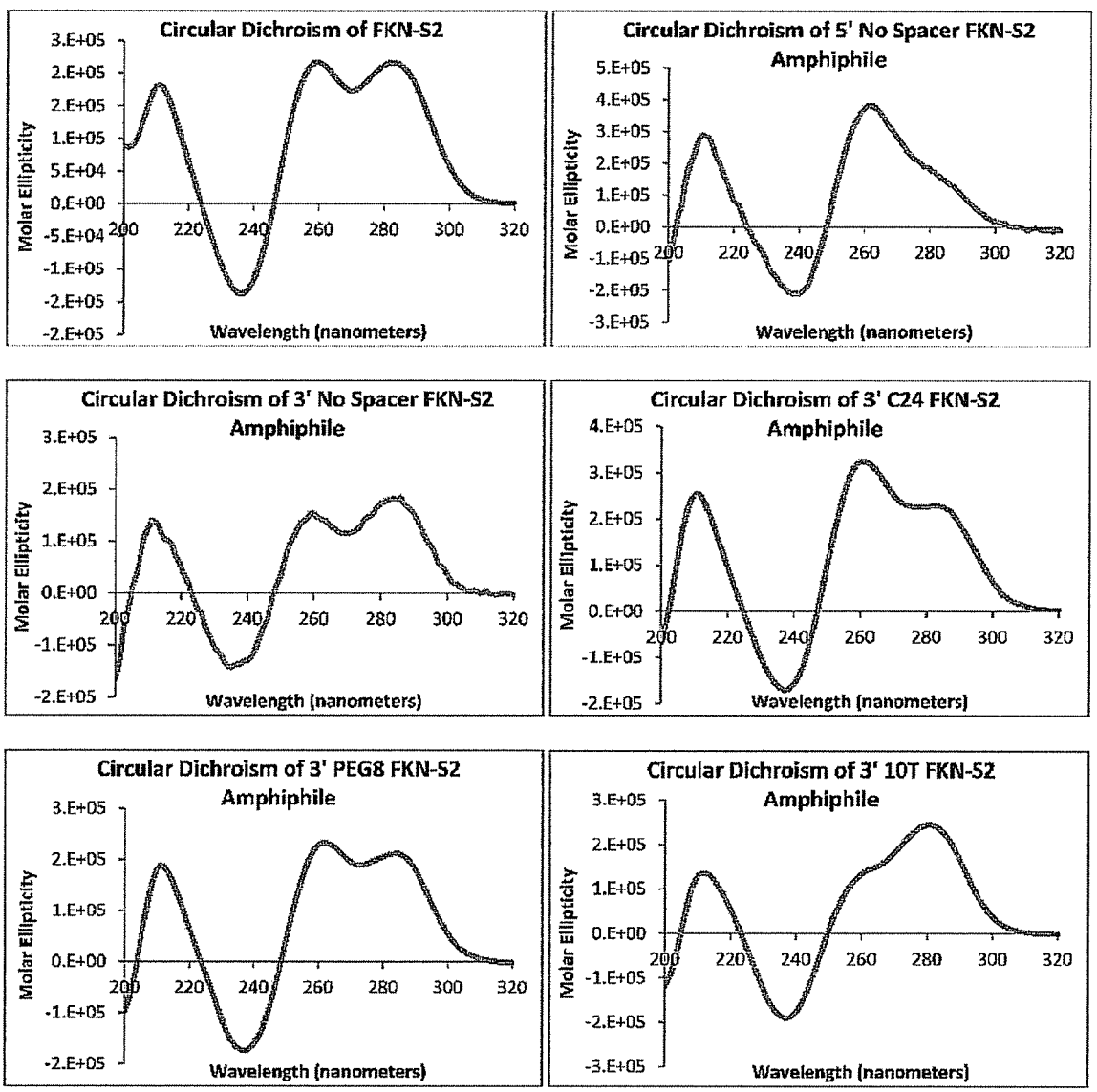
FIG. 17. Circular dichroism spectra of selected spacers.

Circular dichroism studies of the FKN-S2 amphiphiles showed peaks at 260 nm and 285 nm which are characteristic of a parallel G-quartet and B-form DNA respectively (FIG. 17). Certain characteristics emerge. First, for unconjugated FKN-S2, the G-quartet and B-form DNA peaks are of near equal intensities. However, for the 5' No Spacer FKN-S2 amphiphile the B-form DNA peak is significantly reduced and the relative peak heights are largely unchanged for the 3' No Spacer FKN-S2 amphiphile. The IC$_{50}$ for the 5' No Spacer FKN-S2 amphiphile is significantly less than the 3' No Spacer FKN-S2 amphiphile suggesting the B-form portion of the FKN-S2 aptamer is needed for strong binding. Similarly, the 3' C24 FKN-S2 amphiphile has a reduced B-form DNA peak and has less affinity for fractalkine. Similarly, the 3' PEG8 FKN-S2 amphiphile has G-quartet and B-form DNA peaks of similar heights and has the highest affinity of all spacers other than the 3' 10T FKN-S2 amphiphiles. The 3' No Spacer FKN-S2 amphiphile has a significantly stronger B-form DNA peak and the 3' 10T FKN-S2 amphiphile has the lowest IC$_{50}$. However, the addition of additional 10 thymidine nucleotides may increase the B-form DNA peak.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated polynucleotide comprising the polynucleotide sequence SEQ ID NO:1 or a sequence having at least 83% identity to SEQ ID NO:1, wherein the isolated polynucleotide binds to fractalkine, wherein the isolated polynucleotide is single stranded, and wherein the isolated polynucleotide comprises at the 5' end, at the 3' end, or at an internal nucleotide a covalently attached tail.

2. The isolated polynucleotide of claim 1 wherein the isolated polynucleotide is deoxyribonucleic acid.

3. The isolated polynucleotide of claim 1 wherein the isolated polynucleotide comprises at least one modification.

4. The isolated polynucleotide of claim 1 wherein the tail comprises an affinity label.

5. The isolated polynucleotide of claim 1 wherein the tail comprises a hydrophilic group or a hydrophobic group.

6. The isolated polynucleotide of claim 1 wherein the tail comprises an amphiphile.

7. A two-dimensional or three-dimensional surface onto which the isolated polynucleotide of claim 1 is attached.

8. The surface of claim 7 wherein the surface is 3-dimensional.

9. A vesicle comprising the isolated polynucleotide of claim 1 on the surface of the vesicle.

10. A composition comprising the isolated polynucleotide of claim 1 and a pharmaceutically acceptable carrier.

11. A method comprising administering the composition of claim 10 to a subject.

12. The method of claim 11 wherein the subject is a human.

13. A 3-dimensional structure comprising a layer, wherein the layer comprises an attached polynucleotide, wherein the polynucleotide comprises the isolated polynucleotide of claim 1.

14. The 3-dimensional structure of claim 13 wherein the 3-dimensional structure is a vesicle.

15. The 3-dimensional structure of claim 13 wherein the layer comprises a lipid or a polymer.

16. The 3-dimensional structure of claim 13 wherein the layer comprises a hydrophilic polymer.

17. The 3-dimensional structure of claim 16 wherein the hydrophilic polymer comprises polyethylene glycol molecules.

18. The 3-dimensional structure of claim 13 wherein the isolated polynucleotide is covalently attached to the layer.

19. The 3-dimensional structure of claim 18 wherein the isolated polynucleotide is covalently attached to two or more surfaces of the 3-dimensional structure.

20. The isolated polynucleotide of claim 1 wherein the isolated polynucleotide comprises a sequence having at least 90% identity to SEQ ID NO:1, wherein the isolated polynucleotide binds to fractalkine.

21. The isolated polynucleotide of claim 1 wherein the isolated polynucleotide comprises a sequence having at least 95% identity to SEQ ID NO:1, wherein the isolated polynucleotide binds to fractalkine.

22. The isolated polynucleotide of claim 1 wherein the isolated polynucleotide comprises the polynucleotide sequence SEQ ID NO:1, wherein the isolated polynucleotide binds to fractalkine.

23. The isolated polynucleotide of claim 1 wherein the isolated polynucleotide further comprises a spacer located between the isolated polynucleotide and the tail.

\* \* \* \* \*